US007588930B2

(12) United States Patent
Paterson et al.

(10) Patent No.: US 7,588,930 B2
(45) Date of Patent: Sep. 15, 2009

(54) COMPOSITIONS AND METHODS FOR ENHANCING THE IMMUNOGENICITY OF ANTIGENS

(75) Inventors: Yvonne Paterson, Philadelphia, PA (US); Christian Peters, Radnor, PA (US); George Gunn, Collegeville, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/835,662

(22) Filed: Apr. 30, 2004

(65) Prior Publication Data

US 2005/0118184 A1    Jun. 2, 2005

Related U.S. Application Data

(63) Continuation-in-part of application No. 10/239,703, filed on Aug. 7, 2003, which is a continuation-in-part of application No. 09/735,450, filed on Dec. 13, 2000, now Pat. No. 6,767,542, which is a continuation-in-part of application No. 09/537,642, filed on Mar. 29, 2000, now Pat. No. 6,855,320.

(51) Int. Cl.
| C12N 1/21 | (2006.01) |
| C12N 15/00 | (2006.01) |
| C12N 15/09 | (2006.01) |
| C07K 14/435 | (2006.01) |
| C07H 21/04 | (2006.01) |
| A61K 38/17 | (2006.01) |
| A61K 39/08 | (2006.01) |

(52) U.S. Cl. ............... 435/252.3; 435/69.1; 435/320.1; 435/810; 424/185.1; 424/190.1; 424/192.1; 424/200.1; 424/277.1; 530/350; 536/23.7

(58) Field of Classification Search .................. None
See application file for complete search history.

(56) References Cited

U.S. PATENT DOCUMENTS

| 4,521,382 | A | 6/1985 | Kessick |
| 4,567,041 | A | 1/1986 | Likhite |
| 4,777,239 | A | 10/1988 | Schoolnik et al. |
| 4,816,253 | A | 3/1989 | Likhite et al. |
| 4,879,213 | A | 11/1989 | Fox et al. |
| 5,262,177 | A | 11/1993 | Brown et al. |
| 5,342,774 | A | 8/1994 | Boon et al. |
| 5,369,008 | A | 11/1994 | Arlinghaus et al. |
| 5,643,599 | A | 7/1997 | Lee et al. |
| 5,681,570 | A | * | 10/1997 | Yang et al. ............. 424/197.11 |
| 5,824,538 | A | 10/1998 | Branstrom et al. |
| 5,830,702 | A | * | 11/1998 | Portnoy et al. ............. 435/69.3 |
| 5,858,682 | A | * | 1/1999 | Gruenwald et al. .......... 435/7.1 |
| 5,876,735 | A | 3/1999 | Reed |
| 5,877,159 | A | 3/1999 | Powell et al. |
| 6,015,567 | A | 1/2000 | Hudziak et al. |
| 6,051,237 | A | 4/2000 | Paterson et al. |
| 6,306,404 | B1 | 10/2001 | LaPosta et al. |
| 6,333,169 | B1 | 12/2001 | Hudziak et al. |
| 6,479,258 | B1 | 11/2002 | Short |
| 6,521,449 | B1 | 2/2003 | Polack et al. |
| 6,565,852 | B1 | 5/2003 | Paterson |
| 6,767,542 | B2 | 7/2004 | Paterson et al. |
| 6,855,320 | B2 | 2/2005 | Paterson |
| 7,135,188 | B2 | 11/2006 | Paterson |
| 2003/0028206 | A1 | 2/2003 | Shiber |
| 2003/0202985 | A1 | 10/2003 | Paterson |
| 2003/0220239 | A1 | 11/2003 | Simard et al. |
| 2004/0228877 | A1 | 11/2004 | Dubensky et al. |
| 2005/0118184 | A1 | 6/2005 | Paterson et al. |
| 2005/0129715 | A1 | 6/2005 | Paterson et al. |
| 2006/0051380 | A1 | 3/2006 | Schulick et al. |
| 2006/0093582 | A1 | 5/2006 | Paterson et al. |
| 2006/0104991 | A1 | 5/2006 | Paterson et al. |
| 2006/0121053 | A1 | 6/2006 | Sweeney et al. |
| 2006/0205067 | A1 | 9/2006 | Paterson et al. |
| 2006/0210540 | A1 | 9/2006 | Paterson et al. |
| 2006/0233835 | A1 | 10/2006 | Paterson et al. |

FOREIGN PATENT DOCUMENTS

| CA | 2 109 176 | 4/1995 |
| EP | 0 902 086 | 3/1999 |
| EP | 0902086 | 3/1999 |
| JP | 63-173594 | 7/1988 |
| JP | 01 178592 | 7/1989 |
| WO | WO 90/12594 | 11/1990 |
| WO | WO 92/20356 | 11/1992 |
| WO | WO 93/15212 | 8/1993 |
| WO | WO 94/17192 | 8/1994 |

(Continued)

OTHER PUBLICATIONS

Guzman et al, Eur J Immunology 28: 1807-1814, 1998.*

(Continued)

Primary Examiner—Phuong Huynh
(74) Attorney, Agent, or Firm—Mark S. Cohen; Pearl Cohen Zedek Latzer, LLP

(57) ABSTRACT

The present invention includes compositions, methods and kits for enhancing the immunogenicity of an antigen via fusion to a Listerial protein. The present invention further encompasses *Listeria* vaccine strains for enhancing the immunogenicity of an antigen.

19 Claims, 11 Drawing Sheets

FOREIGN PATENT DOCUMENTS

| WO | WO 96/14087 | 5/1996 |
|----|-------------|--------|
| WO | WO 96/34631 | 11/1996 |
| WO | WO 98/48026 | 10/1998 |
| WO | WO 9848026 | 10/1998 |
| WO | WO 99/06544 | 2/1999 |
| WO | WO 99/07861 | 2/1999 |
| WO | WO 99/10496 | 3/1999 |
| WO | WO 99/25376 | 5/1999 |
| WO | WO 01/27295 | 4/2001 |
| WO | WO 01/72329 | 10/2001 |
| WO | WO 03/015716 | 2/2003 |
| WO | WO 03/092600 | 11/2003 |
| WO | WO 03092600 | 11/2003 |
| WO | WO 2004/006837 | 1/2004 |
| WO | WO 2004006837 | 12/2004 |
| WO | WO 2006/036550 | 4/2006 |
| WO | WO 2007/061848 | 5/2007 |
| WO | WO 2007/106476 | 9/2007 |
| WO | WO 2007/130455 | 11/2007 |

OTHER PUBLICATIONS

Attwood et al, The Babel of Bioinformatics, 2000, Science vol. 290 No. 5491: 471-473.*
Finn et al, Nature Reviews Immunolgoy 3: 630-641, Aug. 2003.*
Sewell et al, Cancer Research 64: 8821-8825, 2004.*
Schnupf et al, Cellular microbiology 8(2): 353-364, 2006.*
Guzman, C.A. et al. (Jun. 1998). "Attenuated *Listeria monocytogenes* Carrier Strains can Deliver an HIV-1 gpI20 T Helper Epitope to MHO Class II-Restricted Human CD4+ T Cells," Eur. J. Immunol. 28:1807-1814.
Lebrun, M. et al. (Aug. 1996). "Internalin Must be on the Bacterial Surface to mediate Entry of *Listeria monocytogenes* into Epithelial Cells," Molecular Microbiology 21:579-592.
Paglia, P. et al. (Jun. 1997). "The Defined Attenuated *Listeria monocytogenes* Ampl2 Mutant is an Effective Oral Vaccine Carrier to Trigger a Long-Lasting Immune Response Against a Mouse Fibrosarcoma," Eur. J. Immunol. 27:1570-1575.
Altwood, et al (2000) "The Babel of Bioinformatics" Science, vol. 290, No. 5491, 471-473.
Boon, et al (2006) "Human T cell responses against melanoma." Annu Rev Immunol. 2006; 24:175-208.
Bourquin, et al (2000) "Myelin oligodendrocyte glycoprotein-DNA vaccination induces antibody-mediated autoaggression in experimental autoimmune encephalomyelitis." Eur J Immunol 30: 3663-3671.
Darji, et al (1997) "Oral Somatic Transgene Vaccination Using Attenuated *S. typhimuurium*." vol. 91, 765-775.
Decatur, et al (2000) "A PEST-like sequence in listeriolysin O essential for *Listeria monocytogenes* pathogenicity." Science, vol. 290, No. 5493, pp. 992-995.
Finn, et al (2003) "Cancer vaccines: between the idea and the reality." Nature Reviews Immunology, 3: 630-641.
Guzman, et al (1998) "Attenuated *Listeria monocytogenes* carrier strains can deliver an HIV-1 gp120 T helper epitope to MHC class II-restricted human CD4+ T cells." European Journal of Immunology 28: 1807-1814.
Ikonomidis, et al (1994) "Delivery of a viral antigen to the class I processing and presentation oathway by *Listeria monocytogenes*." Journal of Experimental Medicine, vol. 180, No. 6, pp. 2209-2218.
Kerksiek (1999) "T cell responses to bacterial infection." Curr Opin. Immunol., vol. 1, No. 4, pp. 400-405.
Lasa, et al (1997) "Identification of two regions in the N-terminal domain of ActA involved in the actin comet tail formation by *Listeria monocytogenes*." EMBO 16(7): 1531-40.
Lebrun, et al (1996) "Internalin must be on the bacterial surface to mediate entry of *Listeria monocytogenes* into epithelial cells." Molecular Microbiology 21(3): 579-592.
Mengaud, et al (1988) "Expression In *Escherichia coli* and Sequence Analysis of the Listeriolysin O Determinant of *Listeria monocytogens*." Infection and Immunity, vol. 56, No. 4, 766-772.

An et al (1996) "A recombinant minigene vaccine containing a nonameric cytoxic-T-Lymphocyte epitope confers limited protection against *Listeria monocytogenes* infection." Infect. Immun, vol. 64, No. 5, pp. 1685-1693.
Bielecki et al (1990) "*Bacillus subtilis* expressing a haemolysin gene from *Listeria monocytogenes* can grow in mammalian cells" Nature, vol. 354, pp. 175-176.
Gentschev et al (1995) "*Salmonella* Strain Secreting Active Listeriolysin Changes Its Intracellular Localization" Infect. Immun., vol. 63: 4202-4205.
Kaufman, et al. (1999) "Impact of intracellular location of and antigen display by intracellular bacteria: implications for vaccine development", J Immunol. Lett, 65 (1-2):81-84.
Kocks et al. (1992) "*L. monocytogenes*-induced actin assembly requires the actA gene product." Cell, vol. 68, No. 3, pp. 521-531.
Lin, et al (1996) "Treatment of Established Tumors with a Novel Vaccine That Enhances Major Histocompatibility Class II Presentation of Tumor Antigen" Cancer Res. 1996 56:21-56: 21-26.
Moriishi et al., "Sequence analysis of the actA gene of *Listeria monocytogenes* isolated from human." Microbiol. Immunol., vol. 42, No. 2, ages 129-132.
Paglia, et al (1997) "The defined attenuated *Listeria monocytogenes* delta mp12 mutant is an effective oral vaccine carrier to trigger a long-lasting immune response against a mouse fibrosarcoma."Eur J Immunol 27: 1570-1575.
Pan, et al (1995) "Regression of established tumors in mice mediated by the oral administration of a recombinant *Listeria monocytogenes* vaccine."Cancer Research 55: 4776- 4779.
Paul, et al (1989) Fundamental Immunology, 987-988.
Rechsteiner, et al (1996) "PEST sequences and regulation by proteolysis."TIBS 21: 267-271.
Shen, H. et al. (Apr. 25, 1995). "Recombinant *Listeria monocytogenes* as a Live Vaccine Vehicle for the Induction of Protective Anti-Viral Cell-Mediated Immunity," Proc. Natl. Acad Sci. USA 92: 3987-3991.
Realini et al (1994)"Proposed roles in protein-protein association and presentation of peptides by MHC class I receptors." FEBS Letters 348: 109-113.
Sirard et al (1997) "Intracytoplasmic delivery of Lidteriolysin 0 by a vaccinal strain of *Bacillus anthracis* induces CD8-mediated protection against *Listeria monocytogenes*." J lmmun., vol. 159, pp. 4435-4443.
Tanabe et al.(1999) "Induction of Protective T Cells against *Listeria monocytogenes* in Mice by Immunization with a Listeriolysin O-Negative Avirulent Strain of Bacteria and Liposome-Encapsulated Listeriolysin O" Infect. lmmun. 67(2):568-575.
Verma et al. (1995) "Delivery of class I and class II MHC-restricted T-cell epitopes of listeriolysin of *Listeria monocytogenes* by attenuated *Salmonella*", Vaccine, vol. 13, No. 2, pp. 142-150.
Wu et al.(1996) "Engineering an intracellular pathway for major histocompatibility complex class II presentation of antigens." Cancer Res. 56: 21-26.
Skoble, J. et al. (Aug. 7, 2000). "Three Regions within ActA Promote Arp2/3 Complex-mediated Actin Nucleation and *Listeria monocytogenes* Motility," The Journal of cell Biology 150(3):527-537.
Smith, G.A. et al. (Sep. 1995). "Asymmetric Distribution of the *Listeria monocytogenes* ActA Protein is Required and Sufficient to Direct Actin-Based Motility," Molecular Microbiology 17:945-951.
Welch, M.D. et al. (Jul. 3, 1998). "Interaction of Human Arp2/3 Complex and the *Listeria monocytogenes* ActA Protein in Actin Filament Nucleation," Science 281:105-108; pa-998020.
Jenson E. R. et al (1997) "Recombinant *Listeria monocytogenes* as a live vaccine vehicle and a probe for studying cell-mediated immunity" Immunological Review, vol. 158, 147-157.
Weiskirch, et al (1997) "*Listeria monocytogenes*: a potent vaccine vector for neoplastic and infectious disease." Immunol. Rev, vol. 158, pp. 159-169.
Makela, et al. (1987) Hand Book of Experimental Immunology, vol. 1, chapter 3, pp. 3.1-3.13.
Mikayama, et al. (1993) "Molecular cloning and functional expression of a CDNA encoding gycosylation-inhibiting factor" Proc. Natl. Acad. Sci. USA 90:10056-10060.

Ngo, et al. (1994) The Protein Folding Problem and Tertiary Structure Prediction 492-495.

Safley, et al. (1991) "Role of Listeriolysin-o (LLO) in the T Lymphocyte response to infection with *Listeria monocytogenes*" *J Immunol.* 146(10):3604-3616.

Shen, et al. .(1998) "*Listeria monocytogenes* as a probe to study cell-mediated immunity" *Curr. Opin. Immunol.* 10(4):450-458.

Skolnick, et al. (2000) "From genes to protein structure and function: novel applications of computational approached in the genomic era" *Trends in Biotech.* 18(1):34-39.

Stryer, et al. (1998) Biochemistry, Third Edition, WH Freeman Company, New York, 31-33.

Adams et al. (1992) "Cre-*lox* recombination in *Escherichia coli* cells. Mechanistic differences from the in vitro reaction." *J. Mol. Biol.* 226:661-673.

Allison et al. (1997) "Cloning and characterization of a *Prevotella melaninogenica* hemolysin." *Infect Immun.* 65(7):2765-71.

Anderson (1998) "Human gene therapy." *Nature.* Apr. 30;392(6679 Suppl):25-30.

Angelakopoulos et al. (2002) "Safety and shedding of an attenuated strain of *Listeria monocytogenes* with a deletion of actA/plcB in adult volunteers: a dose escalation study of oral inoculation." *Infect Immun.* 70(7):3592-601.

Awwad (1989) "Cyclophosphamide-induced immunologically mediated regression of a cyclophosphamide-resistant murine tumor: a consequence of eliminating precursor L3T4+ suppressor T-cells." *Cancer Res.* 49(7): 1649-1654.

Barry et al. (1992) "Pathogenicity and immunogenicity of *Listeria monocytogenes* small-plaque mutants defective for intracellular growth and cell-to-cell spread." *Infection and Immunity* 60 (4): 1625-32.

Bast et al. (1975) "Antitumor activity of bacterial infection. II. effect of *Listeria monocytogenes* on growth of a guinea pig hepatoma." *J Natl. Cancer Inst.*, 54(3): 757-761.

Bear (1986) "Tumor-specific suppressor T-cells which inhibit the in vitro generation of cytolytic T-cells from immune and early tumor-bearing host spleens." *Cancer Res.* April;46(4 Pt 1):1805-12.

Beatly. Dissertation Abstracts International, 2000, 61/10B:5224 Abstract Only.

Bernhard et al. (2002) "Vaccination against the HER-2/neu oncogenic protein." *Endocrine-Related Cancer*, 9:33-44.

Billington et al. (1997) "The Arcanobacterium (Actinomyces) pyogenes hemolysin, pyolysin, is a novel member of the thiol-activated cytolysin family." *J Bacteriol.* October;179(19):6100-6.

Bodmer at al. (1988) "Enhanced recognition of a modified peptide antigen by cytotoxic T cells specific for influenza nucleoprotein." *Cell* 52: 253-258.

Boyer et al. (2005) "DNA prime *Listeria* boost induces a cellular immune response to SIV antigens in the rhesus macaque model that is capable of limited suppression of SIV239 viral replication." *Virology.* Mar. 1:333(1):88-101.

Brasseur et al. (1992) "Human gene MAGE-1, which codes for a tumor-rejection antigen, is expressed by some breast tumors." *Int. J Cancer* 52(5):839-841.

Brockstedt et al. (2004) "*Listeria*-based cancer vaccines that segregate immunogenicity from toxicity." *Proc Natl Acad Sci USA.* 101(38):13832-7.

Bron et al. (2004) "Identification of *Lactobacillus plantarum* genes that are induced in the gastrointestinal tract of mice." *J Bacteriol.* September;186(17):5721-9.

Brown et al. (1988) "Site-specific integration in *Saccharopolyspora erythraea* and multisite integration in *Streptomyces lividans* of actinomycete plasmid pSE101." *J. Bacteriology* 170: 2287-2295.

Bruhn et al. (2005) "Characterization of anti-self CD8 T-cell responses stimulated by recombinant *Listeria monocytogenes* expressing the melanoma antigen TRP-2." *Vaccine.* Jul. 21;23(33):4263-72.

Brundage et al. (1993) "Expression and phosphorylation of the *Listeria monocytogenes* ActA protein in mammalian cells." *Proc. Natl. Acad. Sci. USA* 90: 11890-11894.

Bubert et al. (1997) "The *Listeria monocytogenes* lap gene as an indicator gene for the study of PrfA-dependent regulation." *Mol Gen Genet.* September;256(1):54-62.

Burnham (2003) "Bad bugs: good for cancer therapy?" *Drug Discovery Today* 8(2):54-55.

Calendar et al. Poster presented at the ISOPOL Meeting 2001, http://64.233.169.104/search?q=cache:mA__uJpQsCrcJ:www.ma.uni-heidelberg.de/inst/imh/download/isopol.doc+Portnoy+lsopol+2001&hl=en&ct=clnk&cd=3&gl=us.

Camilli et al. (1993) "Dual roles of plcA in *Listeria monocytogenes* pathogenesis." *Mol. Microbiol.* 8:143-157.

Carbone (1989) "Induction of ovalbumin-specific cytotoxic T cells by in vivo peptide immunization." *J Exp Med* 169:603-612.

Carbone (1990) "Class I-restricted processing and presentation of exogenous cell-associated antigen in vivo." *J Exp Med* 171:377-387.

Chamberlain et al. (2000) "Innovations and strategies for the development of anticancer vaccines." *Expert Opinion on Pharmacotherapy* 1(4):603-614.

Courvalin et al. (1995) "Gene transfer from bacteria to mammalian cells." *C R Acad Sci III.* December;318(12):1207-12.

Cunto-Amesty et al. (2003) "Strategies in cancer vaccines development." *Int J Parasitol.* 33(5-6):597-613.

Dakappagari et al. (2000) "Prevention of mammary tumors with a chimeric HER-2 B-cell epitope peptide vaccine." *Cancer Res.* Jul. 15;60(14):3782-9.

Darji et al. (2003) "Induction of immune responses by attenuated isogenic mutant strains of *Listeria monocytogenes.*" *Vaccine* 1;21 Suppl 2:S102-9.

Darji et al. (1995) "Hyperexpression of listeriolysin in the nonpathogenic species *Listeria innocua* and high yield purification." *J Biotechnol.* Dec. 15;43(3):205-12.

Darji et al. (1995) "Listeriolysin generates a route for the presentation of exogenous antigens by major histocompatibility complex class I." *Eur J Immunol.* October;25(10):2967-71.

Darji et al. (1997) "TAP-dependent major histocompatibility complex class I presentation of soluble proteins using listeriolysin." *Eur J Immunol.* June;27(6):1353-9.

Dermime et al. (2004) "Vaccine and antibody-directed T cell tumour immunotherapy." *Biochim Biophys Acta.* 1704(1):11-35.

Deshpande et al. (1997) "Isolation of a contact-dependent haemolysin from *Mycobacterium tuberculosis.*" *J Med Microbiol.* March;46(3):233-8.

Dietrich et al. (1998) "Delivery of antigen-encoding plasmid DNA into the cytosol of macrophages by attenuated suicide *Listeria monocytogenes*" *Nature Biotechnology* 15:181-185.

Dietrich et al. (2001) "From evil to good: a cytolysin in vaccine development." *Trends Microbiol.* January;9(1):23-8.

Dramsi et al. (1995) "Entry of *Listeria monocytogenes* into hepatocytes requires expression of inlB, a surface protein of the internalin multigene family." *Mol Microbiol.* 16(2):251-61.

Dunn et al. (1991) "Selective radiation resistance of immunologically induced T cells as the basis for irradiation-induced T-cell-mediated regression of immunogenic tumor." *J Leukoc Biol.* 49(4): 388-396.

Ebert et al. (1990) "Selective immunosuppressive action of a factor produced by colon cancer cells." *Cancer Res.* 50(19): 6158-6161.

Ezzel (1995) "Cancer Vaccines: An Idea Whose Time Has Come?" J. NIH Res., 7:46-49.

Falk et al. (1991) "Identification of naturally processed viral nonapeptides allows their quantification in infected cells and suggests an allele-specific T cell epitope forecast." *J Exp Med.* 174(2):425-434.

Frankel et al. (1995) "Induction of cell-mediated immune responses to human immunodeficiency virus type 1 Gag protein by using *Listeria monocytogenes* as a live vaccine vector." *J. Immunol.* 155:4775-4782.

Frey (1993) "Rat adenocarcinoma 13762 expresses tumor rejection antigens but tumor-bearing animals exhibit tumor-specific immunosuppression." *Clin Immunol Immunopathol.* 69(2):223-233.

Friedman et al. (2000) "Induction of human immunodeficiency virus (HIV)-specific CD8 T-cell responses by *Listeria monocytogenes* and a hyperattenuated *Listeria* strain engineered to express HIV antigens." *J. Virology* 74 9987-9993.

Fu et al. (1990) "Expansion of immunoregulatory macrophages by granulocyte-macrophage colony-stimulating factor derived from a murine mammary tumor." *Cancer Res.* 50(2):227-234.

Fujii (1987) "Significance of suppressor macrophages for immunosurveillance of tumor-bearing mice." *J Natl Cancer Inst.* 78(3):509-517.

Furukawa (1993) "Nude mouse metastatic models of human stomach cancer constructed using orthotopic implantation of histologically intact tissue." *Cancer Res.* 53(5):1204-1208.

Galen et al. (2001) "Can a 'flawless' live vector vaccine strain be engineered?" *Trends Microbiol.* 9(8):372-6.

Gentschev et al. (1998) "Development of antigen-delivery systems, based on the *Escherichia coli* hemolysin secreatiohn pathway." *Gene* 179:133-140.

Gilmore et al. (1989) "A *Bacillus cereus* cytolytic determinant, cereolysin AB, which comprises the phospholipase C and sphingomyelinase genes: nucleotide sequence and genetic linkage." *J Bacteriol.* February;171(2):744-53.

Glomski et al. (2002) "The *Listeria monocytogenes* hemolysin has an acidic pH optimum to compartmentalize activity and prevent damage to infected host cells." *J Cell Biol.* Mar. 18;156(6)1029-38.

Goebel et al. (1993) "*Listeria monocytogenes*—a model system for studying the pathomechanisms of an intracellular microorganism." *Zbl. Bakt.* 278:334-347.

Goossens et al. (1992) "Induction of protective CD8+ T lymphocytes by an attenuated *Listeria monocytogenes* actA mutant." *Int Immunol.* December;4(12):1413-8.

Goossens et al. (1995) "Attenuated *Listeria monocytogenes* as a live vector for induction of CD8+ T cells in vivo: a study with the nucleoprotein of the lymphocytic choriomeningitis virus." *Int Immunol.* May;7(5):797-805.

Gregory et al. (1997) "Internalin B promotes the replication of *Listeria monocytogenes* in mouse hepatocytes". *Infect Immun.* 65(12):5137-41.

Gunn (2001) "Two *Listeria monocytogenes* vaccine vectors that express different molecular forms of human papilloma virus-16 (HPV-16) E7 induce qualitatively different T cell immunity that correlates with their ability to induce regression of established tumors immortalized by HPV-16." *J Immunol.* 167(11) 6471-6479.

Gunn et al. (2002) "Recombinant Intra-cellular Bacteria as Carriers for Tumor Antigens." In *Vaccine Delivery Strategies*, Chapter 14, Eds. Guido Dietrich and Werner Goebel, Horizon Scientific Press, UK.

Gunn, Dissertation Abstracts International, 2001, 62/5B:2244 Abstract Only.

Gunn et al. (2001) "Listeriolysin—a useful cytolysin." Trends Microbiol.9(4):161-162.

Harty et al. (1996) "Primary and secondary immune responses to *Listeria monocytogenes*." *Curr Opin Immunol.* 8:526-530.

Hassan et al. (2004) "Mesothelin: a new target for immunotherapy." *Clin Cancer Res.* 10(12 Pt 1):3937-42.

Hauf et al. (1997) "*Listeria monocytogenes* infection of P388D1 macrophages results in a biphasic NF-kappaB (RelA/p50) activation induced by lipoteichoic acid and bacterial phospholipases and mediated by IkappaBalpha and IkappaBbeta degradation." *Proc Natl Acad Sci U S A.* Aug. 19;94(17):9394-9.

Hess et al. (1995) "*Listeria monocytogenes* p60 supports host cell invasion by and in vivo survival of attenuated *Salmonella typhimurium.*" *Infect Immun.* May;63(5):2047-53.

Hess et al. (1996) "*Salmonella typhimurium* aroA- infection in gene-targeted immunodeficient mice: major role of CD4+ TCR-alpha beta cells and IFN-gamma in bacterial clearance independent of intracellular location." *J immunol.* May 1;156(9):3321-6.

Hess et al. (1996) "Superior efficacy of secreted over somatic antigen display in recombinant *Salmonella* vaccine induced protection against listeriosis" *Proc. Nat. Acad. Sci.* 93:1458-1463.

Hess et al. (1997) "Protection against murine listeriosis by an attenuated recombinant *Salmonella typhimurium* vaccine strain that secretes the naturally somatic antigen superoxide dismutase." *Infect Immun.* April;65(4):1286-92.

Hess at al. (1998) "*Mycobacterium bovis* bacilli Calmette-Guerin strains secreting listeriolysin of *Listeria monocytogenes*" *Proc. Natl. Acad. Sci.* 95:5299-5304.

Higgins et al. (1998) "Bacterial delivery of DNA evolves." *Nat Biotechnol.* February;16(2):138-9.

Hodgson (2000) "Generalized transduction of serotype 1/2 and serotype 4b strains of *Listeria monocytogenes.*" *Mol Microbiol.* 35(2):312-23.

Hu et al. (2004) "*Escherichia coli* expressing recombinant antigen and listeriolysin O stimulate class I-restricted CD8+ T cells following uptake by human APC." *J. Immunology* 172:1595-1601.

Huang et al. (1994) "Role of bone marrow-derived cells in presenting MHC class I-restricted tumor antigens." *Science* 264961-965.

Hussain et al. (2004) "CD4+CD25+ regulatory T cells that secrete TGFbeta and IL-10 are preferentially induced by a vaccine vector." *J Immunother.* September-October:27(5):339-46.

Ikonomidis et al. (1994) Abstract E-90, Abstracts, 94th General Meeting of the American Society for Microbiology, May 23-27.

Jensen (1997) "Recombinant *Listeria monocytogenes* vaccination eliminates papillomavirus-induced tumors and prevents papilloma formation from viral DNA." *J Virol.* 71(11):8467-8474.

Jones et al. (1994) "Characterization of *Listeria monocytogenes* pathogenesis in a strain expressing perfringolysin O in place of listeriolysin O." *Infect. Immun.* 62:5608-5613.

Kovacsovics-Bankowski et al. (1993) "Efficient major histocompatibility complex class I presentation of exogenous antigen upon phagocytosis by macrophages." *Proc. Natl. Acad. Sci. USA* 90:4942-4946.

Lamikanra et al. (2001) "Regression of established human papillomavirus type 16 (HPV-16) immortalized tumors in vivo by vaccinia viruses expressing different forms of HPV-16 E7 correlates with enhanced CD8(+) T-cell responses that home to the tumor site." *J. Virology* 75(20):9654-9664.

Lampson et al. (1993) "Exploiting the lacZ reporter gene for quantitative analysis of disseminated tumor growth within the brain: use of the lacZ gene product as a tumor antigen, for evaluation of antigenic modulation, and to facilitate image analysis of tumor growth in situ." *Cancer Research* 53:176-182.

Lara-Tejero et al. (2004) "T cell responses to *Listeria monocytogenes.*" *Curr Opin Microbiol.* 7(1):45-50.

Lauer et al. (2002) "Construction, characterization, and use of two *Listeria monocytogenes* site-specific phage integration vectors." *J. Bacteriology* 184: 4177-4186.

Lauer et al. ASM Meeting, Abstract 1999.

Leão et al. (1995) "A species-specific nucleotide sequence of *Mycobacterium tuberculosis* encodes a protein that exhibits hemolytic activity when expressed in *Escherichia coli.*" *Infect Immun.* November;63(11):4301-6.

Lee et al. (1991) "Construction of single-copy integration vectors for *Staphylococcus aureus.*" *Gene* 103:101-5.

Lehner et al. (1996) "Processing and delivery of peptides presented by MHC class I molecules." *Curr Opin Immunol.* 8(1):59-67.

Lejeune (1994) "Nitric oxide involvement in tumor-induced immunosuppression." *J Immunol.* 152(10):5077-5083.

Liau et al. (2002) "Tumor immunity within the central nervous system stimulated by recombinant *Listeria monocytogenes* vaccination." *Cancer Res.* 62(8):2287-93.

Lin et al. (2002) "Oral vaccination with recombinant *Listeria monocytogenes* expressing human papillomavirus type 16 E7 can cause tumor growth in mice to regress." *Int J Cancer.* Dec. 20;102(6):629-37.

Lingnau et al. (1995) "Expression of the *Listeria monocytogenes* EGD inlA and inlB genes, whose products mediate bacterial entry into tissue culture cell lines, by PrfA-dependent and -independent mechanisms." *Infect Immun.* October;63(10):3896-903.

Loeffler et al. (2006) "Comparison of different live vaccine strategies in vivo for delivery of protein antigen or antigen-encoding DNA and mRNA by virulence-attenuated *Listeria monocytogenes.*" *Infect Immun.* July;74(7):3946-57.

Loessner et al. (1995) "Heterogeneous endolysins in *Listeria monocytogenes* bacteriophages: a new class of enzymes and evidence for conserved holin genes within the siphoviral lysis cassettes." *Mol Microbiol.* June;16(6):1231-41.

Loessner et al. (2000) "Complete nucleotide sequence, molecular analysis and genome structure of bacteriophage A118 of *Listeria monocytogenes*: implications for phage evolution." *Molecular Microbiology* 35(2):324-40.

Mandal et al. (2002) "Listeriolysin O-liposome-mediated cytosolic delivery of macromolecule antigen in vivo: enhancement of antigen-specific cytotoxic T lymphocyte frequency, activity, and tumor protection." *BBA* 1563 7-17.

Manjili et al. (2003) "HSP110-HER2/neu chaperone complex vaccine induces protective immunity against spontaneous mammary tumors in HER-2/neu transgenic mice." *J immunol*. Oct. 15;171(8):4054-61.

Marquis et al. (1997) "Proteolytic pathways of activation and degradation of a bacterial phospholipase C during intracellular infection by *Listeria monocytogenes*." *J. Cell Biol*. 137:1381-1392.

Martin et al. (1986) "Nucleotide sequence of the tetM tetracycline resistance determinant of the streptococcal conjugative shuttle transposon Tn1545." *Nucleic Acid Res*. 14:7047-7058.

Marx et al. (2002) "Broad-host-range cre-lox system for antibiotic marker recycling in gram-negative bacteria." *Biotechniques*. November;33(5):1062-7.

McLaughlan et al. (1998) "Molecular characterization of an autolytic amidase of *Listeria monocytogenes* EGD." *Microbiology*. May:144(Pt 5):1359-67.

Mlynárová et al. (2002) "The promiscuity of heterospecific lox sites increases dramatically in the presence of palindromic DNA." *Gene*. Aug. 21;296(1-2):129-37.

Mollet et al. (1993) "Directed genomic integration, gene replacement, and integrative gene expression in *Streptococcus thermophilus*." *J. Bacteriology* 175:4315-4324.

Ochsenbein et al. (1999) "A comparison of T cell memory against the same antigen induced by virus versus intracellular bacteria." *Proc Natl Acad Sci U S A*. Aug. 3;96(16):9293-8.

Oscarsson et al. (1996) "Induction of haemolytic activity in *Escherichia coli* by the slyA gene product." *Mol Microbiol*. April;20(1):191-9.

Palmeros et al. (2000) "A family of removable cassettes designed to obtain antibiotic-resistance-free genomic modifications of *Escherichia coli* and other bacteria." *Gene*. Apr. 18;247(1-2):255-64.

Pan (1999) "Regression of established B16F10 melanoma with a recombinant *Listeria monocytogenes* vaccine." *Cancer Res* 59(20):5264-5269.

Pan et al. (1995) "A recombinant *Listeria monocytogenes* vaccine expressing a model tumour antigen protects mice against lethal tumour cell challenge and causes regression of established tumours." *Nature Med*. 1:471-477.

Parida et al. (1998) "Internalin B is essential for adhesion and mediates the invasion of *Listeria monocytogenes* into human endothelial cells." *Mol Microbiol*. April;28(1):81-93.

Peng et al. (2004) "The ability of two *Listeria monocytogenes* vaccines targeting human papillomavirus-16 E7 to induce an antitumor response correlates with myeloid dendritic cell function." *J. Immunol*. 172:6030-6038.

Penichet et al. (2001) "Antibody-cytokine fusion proteins for the therapy of cancer." *J. Immunological Methods* 248:91-101.

Peters et al. (2003) "Tailoring host immune responses to *Listeria* by manipulation of virulence genes—the interface between innate and acquired immunity." *FEMS Immunol Med Microbiol*. Apr. 1;35(3):243-53.

Pfeifer at al. (1993) "Phagocytic processing of bacterial antigens for class I MHC presentation to T cells." *Nature*. Jan. 28;361(6410):359-62.

Pupa et al. (2001) "Prevention of spontaneous neu-expressing mammary tumor development in mice transgenic for rat proto-neu by DNA vaccination." *Gene Ther*. January;8(1):75-9.

Quénée et al. (2005) "Combined sacB-based negative selection and cre-lox antibiotic marker recycling for efficient gene deletion in *Pseudomonas aeruginosa*." *Biotechniques*. January;38(1):63-7.

Radford et al. (2002) "A recombinant *E. coli* vaccine to promote MHC class I-dependent antigen presentation: application to cancer immunotherapy." *Gene Therapy* 9:1455-1463.

Radford et al. (2003) "Recombinant *E. coli* efficiently delivers antigen and maturation signals to human dendritic cells: presentation of MART1 to CD8+ T cells." *Int. J. Cancer* 105:811-819.

Raveneau et al. (1992) "Reduced virulence of a *Listeria monocytogenes* phospholipase-deficient mutant obtained by transposon insertion into the zinc metalloprotease gene." *Infect. Immun*. 60: 916-921.

Reiter et al. (1989) "Transfer RNA genes frequently serve as integration sites for prokaryotic genetic elements." *Nucleic Acids Research* 17(5)1907-14.

Renard et al. (2003) "HER-2 DNA and protein vaccines containing potent Th cell epitopes induce distinct protective and therapeutic antitumor responses in HER-2 transgenic mice." *J Immunol*. 171(3):1588-95.

Repique (1992) "Immunosuppression derived from human B-lymphoblastoid and melanoma cell lines." *Cancer Invest*. 10(3):201-208.

Roden et al. (2004) "Vaccination to prevent and treat cervical cancer." *Hum Pathol* 35(8):971-82.

Rüssmann et al. (1998) "Delivery of epitopes by the *Salmonella* type III secretion system for vaccine development." *Science*. Jul. 24:281(5376):565-8.

Schafer et al. (1992) "Induction of a cellular immune response to a foreign antigen by a recombinant *Listeria monocytogenes* vaccine." *J. Immunol*. 149(1):53-59.

Scheirlinck et al. (1989) "Integration and expression of alpha-amylase and endoglucanase genes in the *Lactobacillus plantarum* chromosome." *Appl Environ Microbiol* 55(9):2130-7.

Schmidt et al. (1995) "Molecular Analysis of the Plasmid-Encoded Hemolysin of *Escherichia coli* O157:H7 Strain EDL 933" *Infection and Immunity*, 63(3):1055-1061.

Scortti et al. (2007) "The PrfA virulence regulon." *Microbes Infect*. August;9(10):1196-207.

Sewell et al. (2004) "Regression of HPV-positive tumors treated with a new *Listeria monocytogenes* vaccine." *Arch Otolaryngol Head Neck Surg* 130:92-97.

Sewell et al. (2004) "Recombinant *Listeria* vaccines containing PEST sequences are potent immune adjuvants for the tumor-associated antigen human papillomavirus-16 E7." *Cancer Res*. Dec. 15;64(24):8821-5.

Shen et al. (1998) "Compartmentalization of bacterial antigens: differential effects on priming of CD8 T cells and protective immunity." *Cell*. Feb. 20;92(4):535-45.

Shetron-Rama et al. (2002) "Intracellular induction of *Listeria monocytogenes* actA expression." *Infect. Immun*. 70:1087-1096.

Shimizu et al. (1994) "Effects of CD4+ and CD8+ T cells in tumor-bearing mice on antibody production." *Cancer Immunol Immunother*. 38(4):272-276.

Singh et al. (2005) "Fusion to Listeriolysin O and delivery by *Listeria monocytogenes* enhances the immunogenicity of HER-2/neu and reveals subdominant epitopes in the FVB/N mouse." *J Immunol*. Sep. 15;175(6):3663-73.

Slifka et al. (1996) "Antiviral cytotoxic T-cell memory by vaccination with recombinant *Listeria monocytogenes*." *J. Virol*. 70(5):2902-10.

Smith et al. (1995) "The two distinct phospholipases C of *Listeria monocytogenes* have overlapping roles in escape from a vacuole and cell-to-cell spread." *Infect. Immun*. 63 4231-4237.

Souders et al. (2006) "In vivo bactofection: *Listeria* can function as a DNA-cancer vaccine." *DNA Cell Biol*. March;25(3):142-51.

Stahl et al. (1984) "Replacement of the *Bacillus subtilis* subtilisin structural gene with an In vitro-derived deletion mutation." *J. Bacteriol* 158:411-418.

Starks et al. (2004) "*Listeria monocytogenes* as a vaccine vector: virulence attenuation or existing antivector immunity does not diminish therapeutic efficacy." *J. Immunology* 173:420-427.

Stitz et al. (1990) "Characterization and immunological properties of influenza A virus nucleoprotein (NP): cell-associated NP isolated from infected cells or viral NP expressed by vaccinia recombinant virus do not confer protection." *J Gen Virol*. 71(Pt 5):1169-1179.

Strugnell et al. (1990) "Stable expression of foreign antigens from the chromosome of *Salmonella typhimurium* vaccine strains." *Gene* 88:57-63.

Sun et al. (1990) "Isolation of *Listeria monocytogenes* small-plaque mutants defective for intracellular growth and cell-to-cell spread." *Infect. Immun*. 58 3770-3778.

Tilney et al. (1989) "Actin filaments and the growth, movement, and spread of the intracellular bacterial parasite, *Listeria monocytogenes.*" *J Cell Biol.* October;109(4 Pt 1):1597-608.

Vasil et al. (1982) "Cloning of a phosphate-regulated hemolysin gene (phospholipase C) from *Pseudomonas aeruginosa.*" *J Bacteriol.* October;152(1):431-40.

Vazquez-Boland et al. (1992) "Nucleotide sequence of the lecithinase operon of *Listeria monocytogenes* and possible role of lecithinase in cell-to-cell spread." *Infect. Immun.* 60:219-230.

Verch et al. (2004) "*Listeria monocytogenes*-based antibiotic resistance gene-free antigen delivery system applicable to other bacterial vectors and DNA vaccines." *Infect Immun.* November;72(11):6418-25.

Walker et al. (1994) "Tumor growth alters T cell and macrophage production of and responsiveness to granulocyte-macrophage colony-stimulating factor: partial dysregulation through interleukin-10." *Cell Immunol.* 154(1):342-357.

Watson et al. (1991) "Splenic macrophages from tumor-bearing mice co-expressing MAC-1 and MAC-2 antigens exert immunoregulatory functions via two distinct mechanisms." *J Leukoc Biol.* 49(2): 126-138.

Wei et al. (2005) "*Listeria monocytogenes* phosphatidylinositol-specific phospholipase C has evolved for virulence by greatly reduced activity on GPI anchors." *Proc. Natl. Acad. Sci. USA* 102: 12927-12931.

Weidt et al. (1994) "CD8+ T lymphocyte-mediated antiviral immunity in mice as a result of injection of recombinant viral proteins." *J Immunol.* Sep. 15;153(6):2554-61.

Wirth et al. (1986) "Highly efficient protoplast transformation system for *Streptococcus faecalis* and a new *Escherichia coli-S. faecalis* shuttle vector." *J Bacteriol.* 165(3):831-6.

Young et al. (1992) "Tumor-derived cytokines induce bone marrow suppressor cells that mediate immunosuppression through transforming growth factor beta." *Cancer Immunol Immunother.* 35(1): 14-18.

Young et al. (1995) "Holins: form and function in bacteriophage lysis." *FEMS Microbiol Rev.* August;17(1-2):191-205.

Zhang et al. (1993) "Functional replacement of the hemolysin A transport signal by a different primary sequence." *Proc Natl Acad Sci U S A.* May 1;90(9):4211-5.

Abachin et al., "Formation of D-alanyl-lipoteichoic acid is required for adhesion and virulence of *Listeria monocytogenes*", Molecular Microbiology, 2002, 43(1), 1-14.

Aggarwal et al., "Oral *Salmonella*: Malaria Circumsporozoite Recombinants Induce Specific CD8+ Cytotoxic T Cells", J. Exp. Med. 1990, 172, 1083-1090.

Alexander et al., "Characterization of an aromatic amino acid-dependent *Listeria monocytogenes* mutant attenuation, persistance, and ability to induce protective immunity in mice", infection and immunity, May 1993, p. 2245-2248.

Amici et al., "DNA vaccination with full-length or truncated Neu induces protective immunity against the development of spontaneous mammary tumors in HER-2/neu transgenic mice", Gene Therapy, 2000, 7, 703-706.

An et al., 1993, "A recombinant minigene vaccine containing a nonameric cytotoxic-T-Lymphocyte epitope confers limited protection against *Listeria monocytogenes* infection", Infect. Immun., vol. 64, No. 5, pp. 1685-1693.

Angelov et al., "Therapeutic vaccine for acute and chronic motor neuron diseases: Implications for amyotrophic lateral sclerosis", PNAS, Apr. 2003, vol. 100, No. 8, 4790-4795.

Anido et al., "Biosynthesis of tumorigenic HER2 C-terminal fragments by alternative initiation of translation", The EMBO Journal, 2006, 25, 3234-3244.

Bai et al., "Antigenic drift as a mechanism for tumor evasion of destruction by cytplytic T lymphocytes", J. Clin. Invest., 2003, 111, 1487-1496.

Bargmann et al., "The neu oncogene encodes an epidermal growth factor receptor-related protein", Nature, vol. 319, Jan. 1986, 226-230.

Bast et al., "Antitumor activity of bacterial infection, I. effect of *Listeria monocytogenes* on growth of a murine fibrosarcoma", J. Natl. Cancer Inst., 54:749-756, 1975.

Baxeranis et al., Immunobiology of HER-2/neu oncoprotein and its potential application in cancer immunotherapy, Cancer Immunol. Immunother., 2004, 53, 166-175.

Beattie et al., "Cloning and characterization of T-cell-reactive protein antigens from *Listeria monocytogenes*", Infect. Immun., Sep. 1990; 58(9):2792-803.

Beatty, "A dual role for IFN-gamma in resolving the balance between tumor progression and regression" Dissertation Abstracts International, 2000, 61/10B:5224 Abstract only.

Bielecki J. et al., "*Bacillus subtilis* expressing a haemolysin gene from *Listeria monocytogenes* can grow in mammalian cells", Nature 1990, 345:175-176.

Biragyn et al., "Models for Lymphoma", Current protocols in immunology, 2001, 20.6,1-20.6.30.

Boon et al., "Tumor Antigens Recognized by T Lymphocytes", Annu. Rev. Immunol 1994,12, 337-365.

Boon et al., 2006, "Human T cell responses against melanoma", Annu. Rev. Immunol. 24:175-208.

Bourquin et al., 2000, "Myelin oligodendrocyte glycoprotein-DNA vaccination induces antibody-mediated autoaggression in experimental autoimmune encephalomyelitis", Eur. J. Immunol., 30:3663-3671.

Bouwer et al., "Acquired immunity to an intracellular pathogen: immunologic recognition of *L. monocytogenes*-infected cells", Aug. 1997;158:137-46.

Bouwer et al., "Cytotoxic-T-lymphocyte responses to epitopes of listeriolysin O and p60 following infection with *Listeria monocytogenes*", Infect. Immun., Jul. 1996; 64(7):2515-22.

Bowie et al., "Deciphering the message in protein sequences: tolerance to amino acid substitutions" Science 247:1306-1310, 1990.

Bron et al., "Use of the alr gene as a food-grade selection marker in lactic acid bacteria", applied and environmental microbiology, Nov. 2002, vol. 68, No. 11, p. 5663-5670.

Bruder et al., "Efficient induction of cytotoxic CD8+ T cells against exogenous proteins: establishment and charcterization of a T cell line specific for the membrane protein ActA of *Listeria monocytogenes*", Eur. J. Immunol., Sep. 1998, 28(9):2630-9.

Brunner et al., "Quantitative assay of the lytic action of immune lymphoid cells on cr-labelled allogeneic target cells in vitro; inhibition by isoantibody and by drugs", Immunology, 1968, 14, 181-196.

Camilli et al., "*Listeria monocytogenes* mutants lacking phosphatidylinositol-specific phospholipase C are avirulent", J. Exp. Med., vol. 173, 751-754, Mar. 1991.

Catic et al., "Introduction of protein or DNA delivered via recombinant *Salmonella typhimurium* into the major histocompatibility complex class I pesentation pathway of macrophages", Microbes Infect., Feb. 1999, 1(2):113-21.

Chazin et al., "Transformation mediated by the human HER-2 gene independent of the epidermal growth factor receptor", Oncogene, 1992, 7, 1859-1866.

Cheever et al., "T-Cell Immunity to Oncogeneic Proteins Including Mutated RAS and Chimeric BCR-ABL", Ann, N.Y. Acad. Sci. 1993, 690:101-112.

Chen et al., "DNA Vaccines Encoding Full-Length or Truncated Neu Induce Protective Immunity against Neu-expressing Mammary Tumors", Cancer Research 58, 1965-1971, May 1, 1998.

Cho et al., "Structure of the extracellular region of HER2 alone and in complex with the herceptin Fab", Nature, vol. 421, Feb. 2003, 756-760.

Ciurea et al., "Viral presistence in vivo through selection of neutralizing antibody-escape variants", PNAS, Mar. 2000, vol. 97, No. 6, 2749-2754.

Cohen, J. "Cancer vaccines get a shot in the arm" Science 262:841-843, Nov. 1993.

Concetti et al., "Autoantibody to P185$^{erbB2/neu}$ oncoprotein by vaccination with xenogenic DNA", Cancer Immunol. Immunother., 1996, 43, 307-315.

Coussens et al., "Tyrosine kinase receptor with extansive homology to EGF receptor shares chromosomal location with neu oncogene", Science, vol. 230, 1132-1139, Dec. 1985.

Darji et al., "Antigen-specific T cell receptor antagonism by antigen-presenting cells treated with the hemolysin of *Lestria monocytogenes*: a novel type of immune escape", Eur. J. Immunol., Jul. 1997; 27(7):1696-703.

Darji et al., "T-cell anergy induced by antigen presenting cells treated with the hemolysin of *Listeria monocytogenes*", Immunol. Lett., Jun. 1997; 57(1-3):33-7.

Darji et al., "The role of the bacterial membrane protein ActA in immunity and protection against *Listeria monocytogenes*", J. Immunol., Sep. 1, 1998; 161(5):2414-20.

Darji et al., 1997, "Oral somatic transgene vaccination using attenuated *S. typhimurium*", Cell 91:765-775.

Decatur et al., "A PEST-like sequence in listeriolysin O essential for *Listeria monocytogenes* pathogenicity", Science, vol. 290, No. 5493, pp. 992-995, Nov. 3, 2000.

Di Carlo et al., "Inhibition of Mammary Carcinogenesis by systemic interleukin 12 or P185$^{neu}$ DNA vaccination in HER-2/new transgenic BALB\c mice", Clinical Cancer Research, Mar. 2001, vol. 7, 830s-837s.

Disis et al., "Effect of dose on Immune Response in Patients vaccinated with an HER-2/neu Intracellular Domain Protein-Based vaccine", Journal of Clinical Oncology, vol. 22, No. 10, May 2004, 1916-1925.

Disis et al., "Generation of T-cell Immunity to the HER-2/neu Protein After Active Immunization with Her-2/neu Peptide-Based Vaccines", J. Clin. Oncol. 20:2624-2632, 2002.

Disis et al., "HER-2/neu protein: A target for antigen-specific immunotherapy of Human Cancer", Adv Cancer Res 71: 343-371, 1997.

Disis et al., "Immunity to the HER-2/neu oncogenic protein", Ciba Found. Symp. 1994 187:198-211.

Disis et al., "Peptide-Based, but not whole protein, vaccines elicit immunity to HER-2/neu, an oncogenic self-protein", The Journal of Immunology, 1996, 156:3151-3158.

Doling et al., "Cytotoxic T-lymphocyte epitopes fused to anthrax toxin induce protective antiviral immunity", Infect. Immun., Jul. 1999, 67(7):3290-6.

Dumitrescu et al., "Understanding breast cancer risk—where do we stand in 2005?", J. Cell. Mol. Med., vol. 9, No. 1, 2005, pp. 208-221.

Dunn et al., "A critical function for type I interferons in cancer immunoediting", vol. 6, No. 7, Jul. 2005, Nature Immunology, 722-729.

Dunn et al., "Cancer immunoediting from immunosurveillance to tumor escape", Nature Immunology, vol. 3, No. 11, Nov. 2002, 991-998.

Dunn et al., "Interferon-γ and cancer Immunoediting", Immunologic Research, 2005, 32/1-3:231-245.

Dunn, "The Immunobiology of cancer Immunosurveillance and Immunoediting", Immunity, Aug. 2004, vol. 21, 137-148.

Ercolini et al., "Recruitment of latent pools of high-avidity CD8+ T cells to the antitumor immune response", JEM, vol. 201, No. 10, May 2005, 1591-1602.

Esserman et al., "Vaccination with the extracellular domain of P185$^{neu}$ prevents mammary tumor development in neu transgenic mice", Cancer Immunol. Immunother., 1999, 47, 337-342.

Fields, "Preparation of antipeptide antibodies- Introduction to peptide synthesis", Current Protocols in Molecular Biology, 2002, 11.15.1-11.15.9.

Finn et al., MUC-1 Epithelial Tumor Mucin-Based Immunity and Cancer Vaccines, Immuno. Rev. 1995, 145:61-89.

Foy et al., "Vaccination with HER-2/neu DNA or protein subunits protects against growth of HER-2/neu—expressing murine tumor", Vaccine, 19, 2001, 2598-2606.

Freshney, "Culture of animal cells—a manual of basic technique", Chapter 1, Second Edition, 1983, 1-6.

Gallo et al., "Xenogeneic immunization in mice using HER2 DNA delivered by an adenoviral vector", Int. J. Cancer, 113, 67-77, 2005.

Gansbacher et al., "Interleukin 2 Gene Transfer into Tumor Cells Abrogates Tumorigenicity and Induces Protective Immunity", J. Exp. Med. 1990, 172, 1217-1224.

Garay-Malpartida et al., "Caspredictor: a new computer-based tool for caspase substrate prediction", Bioinformatics, vol. 21, suppl. 1, 2005, p. 169-176.

Garcia-Lora et al., "MHC class I-deficient metastatic tumor variants immunoselected by T lymphocytes originate from the corrdinated downregulation of Apm components", Int. J. Cancer, 106, 521-527, 2003.

Gentschev et al., "*Salmonella* Strain Secreting Active Listeriolysin Changes Its Intracellular Localization", Infect. Immun., 1995 63:4202-4205.

Gergory et al., 1997, "Internalin B promotes the replication of *Listeria monocytogenes* in mouse hepatocytes", Infect. Immun. 65(12):5137-41.

Gillespie et al., "The potential of melanoma antigen expression in cancer therapy", Cancer Treat. Rev. 1999, 25(4):219-27.

Glenting et al., "A plasmid selection system in *Lactococcus lactis* and its use for gene expression in *L lactis* and Iluman kidney fibroblasts", Applied and environmental microbiology, Oct. 2002, vol. 68, No. 10, p. 5051-5056.

Golsteyn et al., "Structural and functional similarities between the human cytoskeletal protein zyxin and the ActA protein of *Listeria monocytogenes*." J. Cell Sci. 110:1893-1906, 1997.

Golumbek et al., "Treatment of Established Renal Cancer by Tumor Cells Engineered to Secrete Interleukin-4", Science 1991, 254, 713-716.

Gritzapis et al., "Vaccination with Human HER-2/neu (435-443) CTL peptide induces effective antitumor immunity against HER-2/neu -Expressing tumor cells in vivo", Cancer res., 66, 10, May 2006, 5452-5460.

Guy et al., "Expression of the neu proto oncogene in the mammary epithelium of transgenic mice induces metastatic disease", Proc. Natl. Acad. Sci. USA, Nov. 1992, vol. 89, pp. 10578-10582.

Harris et al., "Molecular Basis for Hetrogeneity of the Human P53 protein", Molecular and Cellular Biology, Dec. 1986, vol. 6, No. 12, p. 4650-4656.

Harty et al., "CD8 T lymphocytes specific for the secreted p60 antigen protect against *Listeria monocytogenes* infection", J. Immunol., May 1, 1995; 154(9):4642-50.

Hess et al., "Live antigen carriers as tools for improved anti-tuberculosis vaccines", FEMS Immunol. Med. Microbiol., Feb. 1999, 23(2), 165-73.

Higgins et al., "Delivery of protein to the cytosol of macrophages using *Escherichia coli* K-12", Mol. Microbiol., Mar. 1999, 31(6):1631-41.

Hiltbold et al., "Mechanisms of processing and presentation of the antigens of *Listeria monocytogenes*", Infect. Agents Dis., Oct. 1993; 2(5):314-23.

Hiltbold et al., "The presentation of class I and class II epitopes of listeriolysin O is regulated by intracellular localization and by intrecellular localization and by intracellular localization and by intracellular spread of *Listeria monocytogenes*", Aug. 1996; 157(3):1163-75.

Hoogenboom et al., "By passing Immunisation—human antibodies from synthetic repertoires of germline $V_H$ gene segments rearranged in vitro", J. Mol. Biol., 1992, 227, 381-388.

Hueman et al., "Phase I clinical trial of a HER-2/neu peptide (E75) vaccine for the prevention of prostate—specific antigen recurrence in high-risk prostate cancer patients", Clin. Cancer Res., 11(20), Oct. 2005, 7470-7479.

Ikonomidis et al., "Delivery of a viral antigen to the class I processing and presentation pathway by *Listeria monocytogenes*", Journal of Experimental Medicine, vol. 180, No. 6, 1994, pp. 2209-2218.

Ikonomidis et al., "Influenza-specific immunity induced by recombinant *Listeria monocytogenes* vaccines", vaccine, vol. 15, No. 4, pp. 433-440, 1997.

Ikonomidis et al., "Recombinant *Listeria monocytogenes* Cancer Vaccines", Vaccines 95, 1995, 95:317-326.

Ikonomidis et al., ASM Las Vegas, the 94$^{th}$ general meeting of the american soceity for microbiology, May 23-27, 1994, Las Vegas convention center, Las Vegas, Nevada, p. 29, 159, 662, 664.

Jensen et al., 1997, "Recombinant *Listeria monocytogenes* as a live vaccine vehicle and a probe for studying cell-mediated immunity", Immunological Review 158:147-157.

Kaufmann et al., "Impact of intracellular location of and antigen display by intracellular bacteria: implications for vaccine development", Immunology Letters 65, 1999, 81-84.

Kawashima et al., "The Multi-epitope Approach for Immunotherapy for Cancer: Identification of Several CTL Epitopes from Various Tumor-Associated Antigens Expressed on Solid Epithelial Tumors", Hum. Immunol. 1998 59:1-14.

Kerksiek et al., "T cell responses to bacterial infection", Curr. Opin. Immunol., vol. 11, No. 4, pp. 400-405, Aug. 1999.

Khong et al., "Identification of multiple antigens recognized by tumor-infiltrating lymphocytes from a single patient: Tumor escape by antigen loss and loss of MHC expression", J. Immunother., 2004, 27, 184-190.

King et al., "Amplification of a Novel v-erbB-related gene in a human mammary carcinoma", Sceince, Sep. 1985, vol. 229, 974-976.

Kocks et al., "*L monocytogenes*-induced act in assembly requires the actA gene of *Listreia monocytogenes* isolated from human", Cell, vol. 68, No. 3, p. 521-531, 1992.

Kohler et al., "Expression of the iap gene coding for protein p60 of *Listeria monocytogenes* is controlled on the posttranseriptional level", Journal of Bacteriology, Aug. 1991, vol. 173, No. 15, p. 4668-4674.

Kruisbeek, "In vivo depletion of CD4- and CD8-specific T cells." Current Protocols in Immunology, John Wiley & Sons, Inc., eds., 1991, V.1, 4.1.1-4.1.2.

Kumar et al., "Amino acid variations at a single residue in an autoimmune peptide profoundly affect its properties: T-cell activation, major histocompatibility complex binding, and ability to block experimental allergic encephalomyelitis" PNAS, 87:1337-1341, 1990.

Kuntson et al., "neu Antigen Negative Variants can be generated after neu-specific antibody therapy in neu transgenic mice", Cancer Research 64, Feb. 2004, 1146-1151.

Kuntson et al., "Immunization with a HER-2/neu helper peptide vaccine generates HER-2/neu CD8 T-cell immunity in cancer patients." The Journal of Clinical Investigation, 107:477-484,2001.

Kyte et al., "A simple method for displaying the hydropathic character of a protein", J. Mol. Biol., 1982, 157, 105-132.

Lacey et al., "Phase IIa safety and immunogenicity of a therapeutic vaccine, TA-GW, in persons with genital warts", The Journal of Infectious Diseases, 1999, 179:612-8.

Lasa et al., 1997, "Identification of two regions in the N-terminal domain of ActA involved in the actin comet tail formation by *Listeria monocytogenes*", EMBO 16(7):1531-40.

Lauer et al., "Systematic mutational analysis of the amino-terminal domain of the *Listeria monocytogenes* ActA protein reveals novel functions in actin-based motility." Molecular Microbiology 42(5):1163-1177, 2001.

Lee et al., "Delivery of macromolecules into cytosol using liposomes containing hemolysin from *Listeria monocytogenes*", J. Biol. Chem., Mar. 29, 1996; 271(13):7249-52.

Lee et al., "The murine MHC class I genes, H-2D and H-2L, and two genes reported to encode tumor-specific antigens", J. Exp. Med., Nov. 1988, vol. 168, 1719-1739.

Leitner et al., "DNA and RNA-based vaccines: prinicples, progress and prospects", Vaccine, Dec. 1999, 18(9-10):765-777.

Lin et al., "Treatment of Established Tumors with a Novel Vaccine that Enhances Major Histocompatibility Class II Presentation of Tumor Antigen", Cancer Res., 1996, 56:21-6.

Lipford et al., "Vaccination with immunodominant peptides encapsulated in Quil A-containing liposomes induces peptide-specific primary CD8+ cytotoxic T cells", Vaccine, Jan. 1994; 12(1):73-80.

Liu, "Vaccine developments", Nature medicine vaccine supplement, May 1998, vol. 4, No. 5, 515-519.

Makela et al., "Haptens and Carriers", Hand book of Experimental Immunology, vol. 1, chapter 3, pp. 3.1.-3.13.; 1987.

Marks et al., "By-Passing Immunization human antibodies from V-gene libraries displayed on phage", J. Mol. Biol. 1991, 222, 581-597.

Mata et al., "Evaluation of a recombinant *Listeria monocytogenes* expressing an HIV protein that protects mice against viral challenge", Vaccine, 19, 2001, 1435-1445.

Mazzaccaro et al., "Major histocompatibility Class I presentation of soluble antigen facilitated by *Mycobacterium tuberculosis* infection", Proc. Natl. Acad. Sci. USA; Oct. 15, 1996; 93(21):11786-91.

McCarty et al., "Targeting p53 for Adoptive T-Cell Immunotherapy", Cancer Research 1998, 15:58 2601-5.

McKaig et al., "Human Papillomavirus and Head and Neck Cancer: Epidemiology and Molecular Biology", Head Neck 1998, 20 (3):250-65.

Mengaud et al., 1988, "Expression in *Escherichia coli* and sequence analysis of the Listeriolysin O determinant of *Listeria monocytogenes*", Infection and Immunity, 56(4):766-772.

Mikayama et al., Molecular cloning and functional expression of a cDNA cncoding gycosylation-inhibiting factor, Nov. 1993, Pro Natl. Acad. Sci., USA, vol. 90:10056-10060.

Miller et al., "Targeted vectors for gene therapy", the FASB Journal, Feb. 1995, vol. 9, p. 190-199.

Moriishi et al., "Sequence analysis of the actA gene of *Listeria monocytogenes* isolated from human", Microbiol. Immunol., vol. 42, No. 2, p. 129-132, 1998.

Muller, "Expression of activated oncogenes in the murine mammary gland: transgenic models for human breast cancer", Cancer and Metastasis Reviews, 10:217-227, 1991.

Murali et al., "Structural analysis of P185$^{C-neu}$ and epidermal growth factor receptor tyrosine kinases: oligomerization of kinase domains", Proc. Natl. Acad. Sci. USA, vol. 93, pp. 6252-6257, Jun. 1996, Biochemistry.

Naz et al., "Novel human prostate-specific cDNA: molecular cloning, expression, and immunobiology of the recombinant protein", Biochemical and Biophysical Research Communications 297, 2002, 1075-1084.

Neeson et al., " A DNA prime-oral *Listeria* boost vaccine in rhesus macaques induces a SIV-specific CD8 T cell mucosal response characterized by high levels of $\alpha 4\beta 7$ integrin and an effector memory phenotype", Virology, Oct. 2006, 354(2), 299-315.

Neeson et al., "Listeriolysin O is an improved protein carrier for lymphoma immunoglobulin idiotype and provides systemic protection against 38c/3 lymphoma", Cancer Immunol. Immunother., 2007, 13 pages.

Ngo et al., 1994,"Computational complexity, protein structure prediction, and the Levinthal paradox", The Protein Folding Problem and Tertiary Structure Prediction, Chptr. 14, pp. 492-495.

Nielsen et al., "Peptide nucleic acids as therapeutic agents", Curr Opin Struc Biol 9(3): 353-7, Jun. 1997.

Pagano, J.S., "Epstein-Barr Virus: The First Human Tumor Virus and its Role in Cancer", Proc. Assoc. Am. Physicians 1999 111(6):573-80.

Pan et al., "Regression of Established Tumors in Mice Mediated by the Oral Administration of a Recombinant *Listeria monocytogenes* vaccine", Cancer Res., 55:4776-4779, Nov. 1995.

Pan et al., "Regression of established B16F10 melanoma with a recombinant *Listeria monocytogenes* vaccine", Cancer Research, 1999, 59:5264-5269.

Pardoll, "Cancer Vaccines", Nature medicine vaccine supplement, May 1998, vol. 4, No. 5, 525-531.

Paterson et al., Proceedings of the American Association for Cancer Research, Mar. 2000, 41:890, abstract # S25.

Paterson, "Rational approaches to immune regulation", Immunogenic Research, 27(2-3):451-462, Jun. 2003.

Paul et al., 1989, "Fundamental Immunology", Second Edition, Raven Press, 987-988.

Piechocki et al., "Complementary Antitumor Immunity Induced by Plasmid DNA Encoding Secreted and Cytoplasmic Human ErbB-2", The Journal of Immunology, 2001, 167:3367-3374.

Pilgrim et al., "Bactofection of mammalian cells by *Listeria monocytogenes*: improvement and mechanism of DNA delivery", Gene Therapy, 2003, 10, 2036-2045.

Pilon et al., "Vaccination with Crytoplasmic ErbB-2 DNA Protects Mice from Mammary Tumor Growth Without Anti-ErbB-2 Antibody", The Journal of Immunology, 2001, 167:3201-3206.

Pricher et al., "Viral escape by selection of cytotoxic T cell-resistant virus variants in vivo" Nature, vol. 346, Aug. 1990, 629-633.

Pucci et al., "*Straphylococcus hameolyticus* contains two D-glutamic acid biosynthetic activities, a glutamate racemase and a D-amino acid transaminase", Journal of Bacteriology, Jan. 1995, vol. 177, No. 2, p. 336-342.

Punwaney et al., "Human Papillomavirus May be Common within Nasopharyngeal Carcinoma of Caucasian Americans: investigation of Epstein-Barr virus and human papillomavirus in Eastern and Western Nasopharyngeal Carcinoma using Ligation-Dependent polymerase chain reaction", Head Neck 1999 21(1):21-9.

Raffaghello et al., "Multiple defects of the antigen-processing machinery components in human neuroblastoma: immunotherapeutic implications", Oncogene, 2005, 24, 4634-4644.

Realini et al., "Proposed roles in protein-protein association and presentation of peptides by MHC class I receptors", FEBS Letters 348, 1994, 109-113.

Rechsteiner et al., 1996, "PEST sequences and regulation by proteolysis", TIBS 21:267-271.

Reilly et al., "HER-2/neu is a tumor rejection target in tolerized HER-2/neu transgenic mice", Cancer research 60, 3569-3576, Jul. 2000.

Restifo et al., "Identification of Human Cancers Deficient in Antigen Processing", J. Exp. Med. 1993, 177, 265-272.

Restifo et al., "The promise of nucleic acid vaccines", Gene Ther., Jan. 2000, 7(2):89-92.

Rogers et al., "Amino acid sequences common to rapidly degraded proteins: the PEST hypothesis", Sceince, Reports, Oct. 1986, vol. 234, 364-368.

Romero et al., "Coordinated downregulation of the anti gen presentation machinery and HLA class I/β2-microglobulin complex is responsible for HLA-ABC loss in bladder cancer", Int. J. Cancer, 2005, 113, 605-610.

Rovero et al., "DNA Vaccination Against Rat Her-2/Neu p185 More Effectively Inhibits Carcinogenesis Than Transplantable Carcinomas in Transgenic BALB/c Mice", The Journal of Immunology, 2000, 165:5133-5142.

Safley et al., "Role of Listeriolysin-o (LLO) in the T lymphocyte response to infection with *Listeria monocytogenes*", J. Immunology, 146(10):3604-3616; May 1991.

Scardino et al., "HER-2/neu and hTERT cryptic epitopes as Novel targets for broad spectrum tumor Immunotherapy", The Journal of Immunology, 2002, 168:5900-5906.

Schlom et al., "Cancer Vaccines:Moving Beyond Current Paradigms", Clin. Cancer Res. 2007; 13(13), Jul. 1, 2007.

Schmidt et al., 1995, "Molecular Analysis of the Plasmid-Encoded Hemolysin of *Escherichia coli* O157:H7 Strain EDL 933", Infection and Immunity, 63(3):1055-1061.

Schneider et al., "Induction of pulmonary allergen-specific IgA responses or airway hyperresponsiveness in the absence of allergic lung disease following sensitization with limiting doses of ovalbumin-alum", Cellular Immunology, 212, 101-109, 2001.

Schwartz, "T cell anergy", Annu. Rev. Immunol., 2003, 21, 305-34.

Seffernick et al., "Melamine deaminase and atrazine chlorohydrolase: 98 percent identical but functionally different." J. Bacteriol. 183(8):2405-10, Apr. 2001.

Serth et al., "Increased Levels of Human Papillomavirus Type 16 DNA in a Subset of Prostate Cancers", Cancer Res., 1999 15:59(4):823-5.

Sewell et al., "Regression of HPV-positive tumors treated with a new *Listeria monocytogenes* vaccine", Arch Otolaryngol Head Neck Surg, Jan. 2004, vol. 130, 92-97.

Shen et al., "*Listeria monocytogenes* as a probe to study cell-mediated immunity", Curr. Opin. Immunol., vol. 10, No. 4, pp. 450-458, Aug. 1998.

Shen et al., 1995, "Recombinant *Listeria monocytogenes* as a live vaccine vehicle for the induction of protective anti-viral cell-mediated immunity", Proc. Nat'l Acad Sci USA 92(9):3987-91.

Shrikant et al., "CTLA-4 blockade reverses CD8+ T cell tolerance to tumor by a CD4+ T cell- and IL-2-dependent mechanism", Immunity, Oct. 1999, vol. 11, 483-493.

Silverman et al., "Expression of c-myc, c-raf-1, and c-Ki-ras in azaserine-induced pancreatic carcinomas and growing pancreas in rats." Mol. Carcinog 3(6):379-86, 1990.

Singh et al., "Structure-Based Design of a Potent, Selective and Irreversible Inhibitor of the Catalytic Domain of the erbB receptor subfamily of protein tyrosine kinases", J. Med. Chem., 1997, 40, 1130-1135.

Singh et al., "Vaccination Strategy Determines the emergence and dominanace of CD8+ T-cell epitopes in a FVB/N Rat HER-2/neu mouse model of breast cancer", Cancer Res., 66, 15, Aug. 2006, 7748-7757.

Sirard et al., "Intrtacytoplasmic delivery of Lidteriolysin O by vaccinal strain of *Bacillus anthracis* induces CD8-mediated protection against *Listeria monocytogenes*", J. Immunology, vol. 159, p. 4435-4443, 1997.

Skolnick et al., From genes to protein structure and function: novel applications of computational approaches in the genomic era, Jan. 2000, Trends in Biotech. 18(1):34-39.

Stover et al., "New Use of BCG for Recombinant Vaccines", Nature 1991, 351, 456-460.

Strych et al., "Mutant analysis shows that alanine racemases from *Pseudomonas aeruginosa* and *Escherichia coli* are dimeric", Journal of Bacteriology, Aug. 2002, p. 4321-4325.

Stryer et al., in Biochemistry, Third Edition, W H Freeman Company, New York, pp. 31-33, 1998.

Szalay et al., "Presentation of *Listeria monocytogenes* antigens by major histocompatibility complex class I molecules to CD8 cytotoxic T lymphocytes independent of listeriolysin secretion and virulence", Eur. J. Immunol., Jul. 1994; 24(7):1471-7.

Tanabe et al., "Induction of Protective T cells against *Listeria monocytogenes* in mice by Immunization with a listeriolysin O-Negative avirulent strain of bacteria and liposome-encapsulated listeriolysin O", Infection and Immunity, Feb. 1999, vol. 67, No. 2, p. 568-575.

Teitelbaum et al., "Mycobacterial infection of macrophages results in membrane-permeable phagosomes", Proc. Natl. Acad. Sci. USA, Dec. 1999; 96(26):15190-5.

Thompson et al., "Pathogenicity and Immunogenicity of a *Listeria monocytogenes* strain that requires D-alaninc for growth", Infection and Immunity, Aug. 1998, vol. 66, No. 8, p. 3552-3561.

Thull et al., "Recognition and management of hereditary breast cancer syndromes", The Oncologist, 2004; 9:13-24.

Townsend et al., "Tumor Rejection after Direct Costimulation of CD8+ T Cells by B7-Transfected Melanoma Cells", Science 1993, 259, 368-370.

Travis, "A Stimulating New Approach to Cancer Treatment", Science 1993, 259, 310-311.

Ulmanen et al., "Transcription and Translation of Foreign genes in *Bacillus subtilis* by the aid of a secretion vector", Journal of Bacteriology, Apr. 1985, vol. 162, No. 1, p. 176-182.

Uyttenhove et al., "Escape of mouse mastocytoma P815 after Nearly complete rejection is due to antigen-loss variants rather than immunosuppression", J. Exp. Med., vol. 157, Mar. 1983, 1040-1052.

Vazquez et al., "Differential regulation of Ia expression and antigen presentation by listeriolysin-producing versus non-producing strains of *Listeria monocytogenes*", J. Leukoc Biol., May 1996; 59(5):683-90.

Verma et al., "Delivery of class I and class II MHC-restricted T-cell epitopes of listeriolysin of *Listeria monocytogenes* by attenuated *Salmonella*", Vacine, vol. 13, No. 2, p. 142-150, Feb. 1995.

Villanueva et al., "Listeriolysin is processed efficiently into an MHC class I-associated epitope in *Listeria monocytogenes*-infected cells", J. Immunol., Dec. 1, 1995; 155(11):5227-33.

Vines et al., "Identification and charcterization of nucleotide sequence difference in there virulence-associate genes of *Listeria monocytogenes* strains representing clinically important serotypes", Current Microbiology, May 1998, vol. 36, No. 5, pp. 309-318.

Vitiello et al., "Development of a Lipopeptide-based Therapeutic Vaccine to treat chronic HBV infection", J. Clin. Invest., vol. 95, Jan. 1995, 341-349.

Watson et al., "Immunosurveillance is active in colorectal cancer as downregulation but not complete loss of MHC class I expression correlates with a poor prognosis", Int. J. Cancer, 2006, 118, 6-10.

Wei et al., "Protection against mammary tumor growth by vaccination with full-length, modified human ErbB-2 DNA", Int. J. Cancer, 81, 748-754, 1999.

Weiskirch et al., "*Listeria monocytogenes*: a potent vaccine vector for neoplastic and infectious disease", Immunol. Rev., vol. 158, Aug. 1997, pp. 159-169.

Wilson et al., "Transient expression of bacterial gene fragments in eukaryotic cells: implications for CD8(+) T cell epitope analysis", J. Immunol. Methods, Feb. 2000, 234(1-2):137-47.

Wingens et al., "Structural analysis of an epidermal growth factor / Transforming growth factor-α chimera with unique ErbB binding specificity", The Journal of Biological Chemistry, vol. 278, No. 40, Issue of Oct. 3, pp. 39114-39123, 2003.

Witkowski et al., "Conversion of a beta-ketoacyl synthase to a malonyl decarboxylase by replacement of the active-site cysteine with glutamine." Biochemistry 38(36):11643-50, Sep. 7, 1999.

Wu et al., "Engineering an intracellular pathway for major histocompatibility complex class II presentation of antigens", Proc. Natl. Acad. Sci. USA, 1995, 92:11671-5.

Wu et al., 1995, "Engineering an intracellular pathway for major histocompatibility complex class II presentation of antigens", Cancer Res. 56:21-26.

Yaghmai et al., "Optimized regulation of gene expression using artificial transcription factors", Molecular Therapy, Jun. 2002, vol. 5, No. 6, 685-694.

Young et al., "Cloning and Expression of Influenza Virus Genes", The Origin of Pandemic Influenza Viruses, W G. Laver, eds., Elsevier Science Publishing Co., Inc., NY, 1983, p. 129.

Zhang et al., "Selection of Tumor Antigens as Targets for Immune Attack Using Immunohistochemistry: Protein Antigens", Clin. Cancer Res. 1998 4:2669-2676.

Zubair et al., In: Vaccines for human Papillomavirus Infection and Anogential Disease (ed. Robert W. Tindle); 1999, pp. 173-192.

Zwickey et al., "Peptide epitopes from noncytosolic *Listeria monocytogenes* can be presented by major histocompatibiity complex class I molecules", Infect. Immun., May 1996; 64(5):1870-2.

Zwickey et al, "Antigen secreted from noncytosolic *Listeria monocytogenes* is processed by the classical MHC class I processing pathway", J. Immunol., Jun. 1999, 162(11):6341-50.

Gunn, "Recombinant listeria monocytogenes as a tumor therapeutic", *Univ. of Pennsylvania - Electronic Dissertations*. Paper AAI3015316, UMI Microform 3015316, 2001, pp. v-vi, Bell and Howell Information and Learning Company, Ann Arbor, Michigan, abstract.

Paterson et at., "Recombinant Listeria monocytogenes cancer vaccines", Curr Opin Immunol. Oct. 1996;8(5) 664-669.

Scortti at al., " The PrfA virulence regulon", Microbes Infect. Aug. 2007;9(10):1196-207. Epub May 7, 2007.

* cited by examiner

SEQUENCE LISTING

<160> NUMBER OF SEQ ID NOS: 24

<210> SEQ ID NO 1
<211> LENGTH: 32
<212> TYPE: PRT
<213> ORGANISM: Listeria monocytogenes

<400> SEQUENCE: 1

Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
            20                  25                  30

<210> SEQ ID NO 2
<211> LENGTH: 14
<212> TYPE: PRT
<213> ORGANISM: Listeria monocytogenes

<400> SEQUENCE: 2

Lys Thr Glu Glu Gln Pro Ser Glu Val Asn Thr Gly Pro Arg
1               5                   10

<210> SEQ ID NO 3
<211> LENGTH: 28
<212> TYPE: PRT
<213> ORGANISM: Listeria monocytogenes

<400> SEQUENCE: 3

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 4
<211> LENGTH: 20
<212> TYPE: PRT
<213> ORGANISM: Listeria monocytogenes

<400> SEQUENCE: 4

Lys Asn Glu Glu Val Asn Ala Ser Asp Phe Pro Pro Pro Pro Thr Asp
1               5                   10                  15

Glu Glu Leu Arg
            20

<210> SEQ ID NO 5
<211> LENGTH: 33
<212> TYPE: PRT
<213> ORGANISM: Listeria monocytogenes

<400> SEQUENCE: 5

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg

<210> SEQ ID NO 6
<211> LENGTH: 17
<212> TYPE: PRT
<213> ORGANISM: Streptococcus pyogenes

<400> SEQUENCE: 6

Lys Gln Asn Thr Ala Ser Thr Glu Thr Thr Thr Thr Asn Glu Gln Pro
1               5                   10                  15

Lys

<210> SEQ ID NO 7
<211> LENGTH: 17
<212> TYPE: PRT
<213> ORGANISM: Streptococcus equisimilis

<400> SEQUENCE: 7

Lys Gln Asn Thr Ala Asn Thr Glu Thr Thr Thr Thr Asn Glu Gln Pro
1               5                   10                  15

Lys

```
<210> SEQ ID NO 8
<211> LENGTH: 27
<212> TYPE: DNA
<213> ORGANISM: Artificial Sequence
<220> FEATURE:
<223> OTHER INFORMATION: PCR Primer

<400> SEQUENCE: 8
gctagccctc ctttgattag tatattc                                           27

<210> SEQ ID NO 9
<211> LENGTH: 36
<212> TYPE: DNA
<213> ORGANISM: Artificial Sequence
<220> FEATURE:
<223> OTHER INFORMATION: PCR Primer

<400> SEQUENCE: 9
gcggatgaaa tcgataagca tggagataca cctaca                                 36

<210> SEQ ID NO 10
<211> LENGTH: 36
<212> TYPE: DNA
<213> ORGANISM: Artificial Sequence
<220> FEATURE:
<223> OTHER INFORMATION: PCR Primer

<400> SEQUENCE: 10
cgcctacttt agctattcgt acctctatgt ggatgt                                 36

<210> SEQ ID NO 11
<211> LENGTH: 20
<212> TYPE: DNA
<213> ORGANISM: Artificial Sequence
<220> FEATURE:
<223> OTHER INFORMATION: PCR Primer

<400> SEQUENCE: 11
gagtctttgg tattgggccc                                                   20

<210> SEQ ID NO 12
<211> LENGTH: 22
<212> TYPE: DNA
<213> ORGANISM: Artificial Sequence
<220> FEATURE:
<223> OTHER INFORMATION: PCR Primer

<400> SEQUENCE: 12
gctctagatt atggtttctg ag                                                22

<210> SEQ ID NO 13
<211> LENGTH: 26
<212> TYPE: DNA
<213> ORGANISM: Artificial Sequence
<220> FEATURE:
<223> OTHER INFORMATION: PCR Primer

<400> SEQUENCE: 13
ggggtaccct cctttgatta gtatat                                            26

<210> SEQ ID NO 14
<211> LENGTH: 31
<212> TYPE: DNA
<213> ORGANISM: Artificial Sequence
```

```
<220> FEATURE:
<223> OTHER INFORMATION: PCR Primer

<400> SEQUENCE: 14
ggggtctaga cctcctttga ttagtatatt c                               31

<210> SEQ ID NO 15
<211> LENGTH: 45
<212> TYPE: DNA
<213> ORGANISM: Artificial Sequence
<220> FEATURE:
<223> OTHER INFORMATION: PCR Primer

<400> SEQUENCE: 15
atcttcgcta tctgtcgccg cggcgcgtgc ttcagtttgt tgcgc                45

<210> SEQ ID NO 16
<211> LENGTH: 45
<212> TYPE: DNA
<213> ORGANISM: Artificial Sequence
<220> FEATURE:
<223> OTHER INFORMATION: PCR Primer

<400> SEQUENCE: 16
gcgcaacaaa ctgaagcagc ggccgcggcg acagatagcg aagat                45

<210> SEQ ID NO 17
<211> LENGTH: 42
<212> TYPE: DNA
<213> ORGANISM: Artificial Sequence
<220> FEATURE:
<223> OTHER INFORMATION: PCR Primer

<400> SEQUENCE: 17
tgtaggtgta tctccatgct cgagagctag gcgatcaatt tc                   42

<210> SEQ ID NO 18
<211> LENGTH: 42
<212> TYPE: DNA
<213> ORGANISM: Artificial Sequence
<220> FEATURE:
<223> OTHER INFORMATION: PCR Primer

<400> SEQUENCE: 18
ggaattgatc gcctagctct cgagcatgga gatacaccta ca                   42

<210> SEQ ID NO 19
<211> LENGTH: 42
<212> TYPE: DNA
<213> ORGANISM: Artificial Sequence
<220> FEATURE:
<223> OTHER INFORMATION: PCR Primer

<400> SEQUENCE: 19
aaacggattt atttagatcc cgggttatgg tttctgagaa ca                   42

<210> SEQ ID NO 20
<211> LENGTH: 42
<212> TYPE: DNA
<213> ORGANISM: Artificial Sequence
<220> FEATURE:
<223> OTHER INFORMATION: PCR Primer

<400> SEQUENCE: 20
tgttctcaga aaccataacc cgggatctaa ataaatccgt tt                   42
```

```
<210> SEQ ID NO 21
<211> LENGTH: 28
<212> TYPE: DNA
<213> ORGANISM: Artificial Sequence
<220> FEATURE:
<223> OTHER INFORMATION: PCR Primer

<400> SEQUENCE: 21
gggggtcgac cagctcttct tggtgaag                                          28

<210> SEQ ID NO 22
<211> LENGTH: 9
<212> TYPE: PRT
<213> ORGANISM: Human papillomavirus

<400> SEQUENCE: 22

Arg Ala His Tyr Asn Ile Val Thr Phe
1               5

<210> SEQ ID NO 23
<211> LENGTH: 390
<212> TYPE: PRT
<213> ORGANISM: Listeria monocytogenes

<400> SEQUENCE: 23

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Glu Lys Thr Glu Glu Gln Pro Ser Glu
        35                  40                  45

Val Asn Thr Gly Pro Arg Tyr Glu Thr Ala Arg Glu Val Ser Ser Arg
    50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95

Ile Asn Asn Asn Asn Ser Glu Gln Thr Glu Asn Ala Ala Ile Asn Glu
            100                 105                 110

Glu Ala Ser Gly Ala Asp Arg Pro Ala Ile Gln Val Glu Arg Arg His
        115                 120                 125

Pro Gly Leu Pro Ser Asp Ser Ala Ala Glu Ile Lys Lys Arg Arg Lys
    130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Lys Val Ala Lys Glu Ser Val Ala
                165                 170                 175

Asp Ala Ser Glu Ser Asp Leu Asp Ser Ser Met Gln Ser Ala Asp Glu
            180                 185                 190

Ser Ser Pro Gln Pro Leu Lys Ala Asn Gln Gln Pro Phe Phe Pro Lys
        195                 200                 205

Val Phe Lys Lys Ile Lys Asp Ala Gly Lys Trp Val Arg Asp Lys Ile
    210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255
```

```
Ser Asp Phe Pro Pro Pro Thr Asp Glu Glu Leu Arg Leu Ala Leu
            260                 265                 270

Pro Glu Thr Pro Met Leu Leu Gly Phe Asn Ala Pro Ala Thr Ser Glu
        275                 280                 285

Pro Ser Ser Phe Glu Phe Pro Pro Pro Thr Asp Glu Glu Leu Arg
        290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Ile Arg Glu Thr Ala Ser Ser Leu Asp Ser Ser Phe
            340                 345                 350

Thr Arg Gly Asp Leu Ala Ser Leu Arg Asn Ala Ile Asn Arg His Ser
        355                 360                 365

Gln Asn Phe Ser Asp Phe Pro Pro Ile Pro Thr Glu Glu Leu Asn
        370                 375                 380

Gly Arg Gly Gly Arg Pro
385                 390
```

<210> SEQ ID NO 24
<211> LENGTH: 1170
<212> TYPE: DNA
<213> ORGANISM: Listeria monocytogenes

<400> SEQUENCE: 24

```
atgcgtgcga tgatggtggt tttcattact gccaattgca ttacgattaa ccccgacata    60
atatttgcag cgacagatag cgaagattct agtctaaaca cagatgaatg ggaagaagaa   120
aaaacagaag agcaaccaag cgaggtaaat acgggaccaa gatacgaaac tgcacgtgaa   180
gtaagttcac gtgatattaa agaactagaa aaatcgaata agtgagaaa tacgaacaaa   240
gcagacctaa tagcaatgtt gaaagaaaaa gcagaaaaag gtccaaatat caataataac   300
aacagtgaac aaactgagaa tgcggctata aatgaagagg cttcaggagc cgaccgacca   360
gctatacaag tggagcgtcg tcatccagga ttgccatcgg atagcgcagc ggaaattaaa   420
aaagaagga agccatagc atcatcggat agtgagcttg aaagccttac ttatccggat   480
aaaccaacaa agtaaataa gaaaaagtg gcgaaagagt cagttgcgga tgcttctgaa   540
agtgacttag attctagcat gcagtcagca gatgagtctt caccacaacc tttaaaagca   600
aaccaacaac catttttccc taaagtattt aaaaaaataa agatgcggg gaaatgggta   660
cgtgataaaa tcgacgaaaa tcctgaagta agaaagcga ttgttgataa aagtgcaggg   720
ttaattgacc aattattaac caaaagaaa agtgaagagg taaatgcttc ggacttcccg   780
ccaccaccta cggatgaaga gttaagactt gctttgccag agacaccaat gcttcttggt   840
tttaatgctc ctgctacatc agaaccgagc tcattcgaat tccaccacc acctacggat   900
gaagagttaa gacttgcttt gccagagacg ccaatgcttc ttggttttaa tgctcctgct   960
acatcggaac cgagctcgtt cgaatttcca ccgcctccaa cagaagatga actagaaatc   1020
atccgggaaa cagcatcctc gctagattct agttttacaa gaggggattt agctagtttg   1080
agaaatgcta ttaatcgcca tagtcaaaat ttctctgatt tcccaccaat cccaacagaa   1140
gaagagttga acgggagagg cggtagacca   1170
```

US 7,588,930 B2

COMPOSITIONS AND METHODS FOR ENHANCING THE IMMUNOGENICITY OF ANTIGENS

CROSS REFERENCE TO RELATED APPLICATIONS

This application is a Continuation-in-Part of co-pending U.S. application Ser. No. 10/239,703, filed Aug. 7, 2003, which is a Continuation-in-Part of U.S. application Ser. No. 09/735,450, filed Dec. 13, 2000, now U.S. Pat. No. 6,767,542, which is a Continuation-in-Part of U.S. application Ser. No. 09/537,642, filed Mar. 29, 2000, now U.S. Pat. No. 6,855,320.

STATEMENT REGARDING FEDERALLY SPONSORED RESEARCH OR DEVELOPMENT

This invention was supported in part by funds from the U.S. government (National Cancer Institute Grant No. CA69632) and the U.S. government may therefore have certain rights in the invention.

BACKGROUND OF THE INVENTION

Stimulation of an immune response is dependent upon the presence of antigens recognized as foreign by the host immune system. Bacterial antigens such as *Salmonella enterica* and *Mycobacterium bovis* BCG remain in the phagosome and stimulate CD4 T-cells via antigen presentation through major histocompatibility class II molecules. In contrast, bacterial antigens such as *Listeria monocytogenes* exit the phagosome into the cytoplasm. The phagolysosomal escape of *L. monocytogenes* is a unique mechanism which facilitates major histocompatibility class I antigen presentation of listerial antigens. This escape is dependent upon the pore-forming sulfhydryl-activated cytolysin, listeriolysin O (LLO).

The ability of *L. monocytogenes* to break down the vacuole within a host cell and enter the cytoplasm has led to its use as a recombinant vaccine. U.S. Pat. No. 5,830,702 describes vaccines comprising attenuated mutants of *Listeria* spp. genetically engineered to express foreign antigens in the cytoplasm of infected macrophages and other cells. Several approaches for expressing the antigen in *Listeria* spp. are described including generation of a fusion protein of a selected foreign antigen and a listerial protein, preferably an enzyme involved in lysis of host vacuoles. In particular, a fusion protein encoding the hly promoter and the first 416 amino acids of LLO fused in-frame to the entire coding sequence of the NP antigen was constructed in *E. coli* and on transformation to *Listeria monocytogenes* secreted a 105 kDA protein that reacts with antiserum to LLO and NP (col. 24 of '702 patent). Recombinant *L. monocytogenes* secreting a fusion protein comprising listeriolysin O and NP (LLO-NP) was demonstrated to target infected cells for lysis by NP-specific class I-restricted cytotoxic T cells. In contrast, a hemolysin-negative *L. monocytogenes* strain expressing LLO-NP presented the antigen in a class II restricted manner (Ikonimidis et al., J. Exp. Med. 1994 180: 2209-2218). Thus, from these studies it was surmised that hemolysin-dependent bacterial escape from the vacuole is necessary for class I presentation in vitro.

The escape function of *L. monocytogenes* has also been transferred to *Bacillus subtilis* and attenuated *Salmonella* sp. strains (Bielecki et al. Nature 1990 354: 175-176, Gentschev et al. Infect. Immun. 1995 63: 4202-4205). *S. enteric* and *M. bovis* BCG vaccine carriers which secrete listeriolysin O have also been constructed (Kaufman, S. H. and Hess, J. Immunol. Lett. January 1999 65: 81-84). These constructs are taught to be capable of introducing antigens into the MHC class II and MHC class I pathway, resulting in stimulation of both CD4 and CD8 T-cells. Comparison of *S. enterica* vaccines which display the same listerial antigen in secreted and somatic form showed the secreted antigen display to be superior to the somatic antigen display (Kaufman, S. H. and Hess, J. Immunol. Lett. January 1999 65(1-2):81-4).

International Publication No. WO 99/10496 discloses recombinant BCG strains secreting hemolytically active hly with an improved MHC class I-restricted immune response for use as a vaccine against tuberculosis.

Administration of purified listeriolysin O encapsulated in liposomes has also been reported to be effective in the induction of antigen-specific Th1-dependent protective immunity to various kinds of intracellular parasitic bacteria in vivo (Tanabe et al. Infect. Immun. February 1999 67: 568-75).

PEST sequences in eukaryotic proteins have long been identified. It has been taught that proteins containing amino acid sequences that are rich in prolines (P), glutamic acids (E), serines (S) and threonines (T), generally, but not always, flanked by clusters containing several positively charged amino acids, have rapid intracellular half-lives (Rogers et al., 1986, Science 234:364-369). Further, it has been shown that these sequences target the protein to the ubiquitin-proteosome pathway for degradation (Rechsteiner and Rogers TIBS 1996 21:267-271). This pathway is also used by eukaryotic cells to generate immunogenic peptides that bind to MHC class I and it has been hypothesized that PEST sequences are abundant among eukaryotic proteins that give rise to immunogenic peptides (Realini et al. FEBS Lett. 1994 348:109-113). Prokaryotic proteins do not normally contain PEST sequences because they do not have this enzymatic pathway. However, a PEST-like sequence rich in the amino acids proline (P), glutamic acid (E), serine (S) and threonine (T) was recently identified at the amino terminus of LLO and demonstrated to be essential for *L. monocytogenes* pathogenicity (Decatur, A. L. and Portnoy, D. A. Science 2000 290:992-995). Decatur and Portnoy teach that the presence of this PEST-like sequence in LLO targets the protein for destruction by proteolytic machinery of the host cell so that once the LLO has served its function and facilitated the escape of *L. monocytogenes* from the phagolysosomal vacuole, it is destroyed before it can damage the cells.

It has now been found that the immune response to an antigen can be enhanced by fusion of the antigen to a non-hemolytic truncated form of listeriolysin O (ΔLLO). It is believed that the observed enhanced cell mediated immunity and anti-tumor immunity of the fusion protein results from the PEST-like sequence present in LLO which targets the antigen for processing.

Another Listerial protein, ActA, comprises PEST and PEST-like sequences. ActA is a surface-associated protein, and acts as a scaffold in infected host cells to facilitate the polymerization, assembly and activation of host actin polymers in order to propel the Listeria organism through the cytoplasm. Shortly after entry into the mammalian cell cytosol, *L. monocytogenes* induces the polymerization of host actin filaments and uses the force generated by actin polymerization to move, first intracellularly and then from cell to cell. A single bacterial protein, ActA is responsible for mediating actin nucleation and actin-based motility. The ActA protein provides multiple binding sites for host cytoskeletal components, thereby acting as a scaffold to assemble the cellular actin polymerization machinery. The $NH_2$ terminus of ActA binds to monomeric actin and acts as a constitutively active nucleation promoting factor by stimulating the intrinsic actin nucleation activity. ActA and hly are both members of the 10-kb gene cluster regulated by the transcriptional activator PrfA, and is upregulated approximately 226-fold in the mammalian cytosol.

There exists a long-felt need to develop compositions and methods to enhance the immunogenicity of antigens, especially antigens useful in the prevention and treatment of tumors and intracellular pathogens. The present invention meets this need.

SUMMARY OF THE INVENTION

The present invention includes a method for enhancing the immunogenicity of an antigen comprising fusing to the antigen a truncated ActA protein, or a fragment thereof.

In one aspect of the present invention, the truncated ActA protein is at least 95% homologous to the sequence set forth in SEQ ID NO:23.

In another aspect of the present invention, the truncated ActA protein, or fragment thereof, comprises the sequence set forth in SEQ ID NO:23.

In still another aspect of the present invention, the truncated ActA protein consists of the sequence set forth in SEQ ID NO:23.

The present invention further includes a vector comprising an isolated nucleic acid encoding a truncated ActA protein, or a fragment thereof, and an isolated nucleic acid encoding an antigen, wherein the isolated nucleic acid encoding a truncated ActA protein has 95% identity to the nucleic acid sequence set forth in SEQ ID NO:24, and further wherein when the isolated nucleic acid encoding a truncated ActA and the isolated nucleic acid encoding an antigen are expressed in a cell, the isolated nucleic acid encoding a truncated ActA and the isolated nucleic acid encoding an antigen are expressed as a fusion protein.

In one aspect of the present invention, the isolated nucleic acid encoding a truncated ActA protein, or fragment thereof, comprises the sequence set forth in SEQ ID NO:24.

In another aspect of the present invention, the isolated nucleic acid encoding a truncated ActA protein, or fragment thereof, consists of the sequence set forth in SEQ ID NO:24.

The present invention further includes a *Listeria* vaccine strain comprising an antigen fused to a truncated ActA protein, or fragment thereof.

In one aspect of the present invention, the truncated ActA protein is at least 95% homologous to the sequence set forth in SEQ ID NO:23.

In another aspect of the present invention, the truncated ActA protein, or fragment thereof, comprises the sequence set forth in SEQ ID NO:23.

In one aspect of the present invention, the truncated ActA protein consists of the sequence set forth in SEQ ID NO:23.

In still another aspect of the present invention, the antigen and the truncated ActA protein, or fragment thereof, are encoded by a vector.

In another aspect of the present invention, the *Listeria* vaccine strain is the species *Listeria monocytogenes*.

The present invention further includes a method of eliciting an enhanced immune response to an antigen, the method comprising administering to a mammal an effective amount of a composition comprising a *Listeria* vaccine strain, wherein the *Listeria* vaccine strain comprises an antigen fused to a truncated ActA protein, or a fragment thereof.

In one aspect of the present invention, the mammal is a human.

In still another aspect of the present invention, the truncated ActA protein is at least 95% homologous to the sequence set forth in SEQ ID NO:23.

In one aspect of the present invention, the truncated ActA protein, or fragment thereof, comprises the sequence set forth in SEQ ID NO:23.

In another aspect of the present invention, the truncated ActA protein consists of the sequence set forth in SEQ ID NO:23.

In still another aspect of the present invention, the composition is suspended in a pharmaceutically acceptable carrier.

The present invention further includes a kit for eliciting an enhanced immune response to an antigen, the kit comprising a *Listeria* vaccine strain, wherein the *Listeria* vaccine strain comprises an antigen fused to a truncated ActA protein, or fragment thereof, and a pharmaceutically acceptable carrier, said kit further comprising an applicator, and an instructional material for use thereof.

The present invention further includes a kit for eliciting an enhanced immune response to an antigen, the kit comprising an antigen fused to a truncated ActA protein, or fragment thereof, and a pharmaceutically acceptable carrier, said kit further comprising an applicator, and an instructional material for use thereof.

The present invention further includes an isolated nucleic acid encoding a truncated ActA protein, or a fragment thereof, and an antigen, wherein said isolated nucleic acid encoding the truncated ActA protein has 95% identity to the nucleic acid sequence set forth in SEQ ID NO:24.

In one aspect of the present invention, the truncated ActA protein, or fragment thereof, comprises the sequence set forth in SEQ ID NO:24.

In another aspect of the present invention, the truncated ActA protein consists of the sequence set forth in SEQ ID NO:24.

The present invention further includes an isolated fusion protein comprising a truncated ActA protein, or a fragment thereof, and an antigen, wherein said isolated fusion protein comprises a truncated ActA protein having 95% identity to the amino acid sequence set forth in SEQ ID NO:23.

In one aspect of the present invention, the truncated ActA protein, or fragment thereof, comprises the sequence set forth in SEQ ID NO:23.

In still another aspect of the present invention, the truncated ActA protein consists of the sequence set forth in SEQ ID NO:23.

In another aspect of the present invention, the fusion protein is suspended in a pharmaceutically acceptable carrier.

In one aspect of the present invention, the fusion protein is suspended in a pharmaceutically acceptable carrier.

In another aspect of the present invention, the fusion protein is suspended in a pharmaceutically acceptable carrier.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
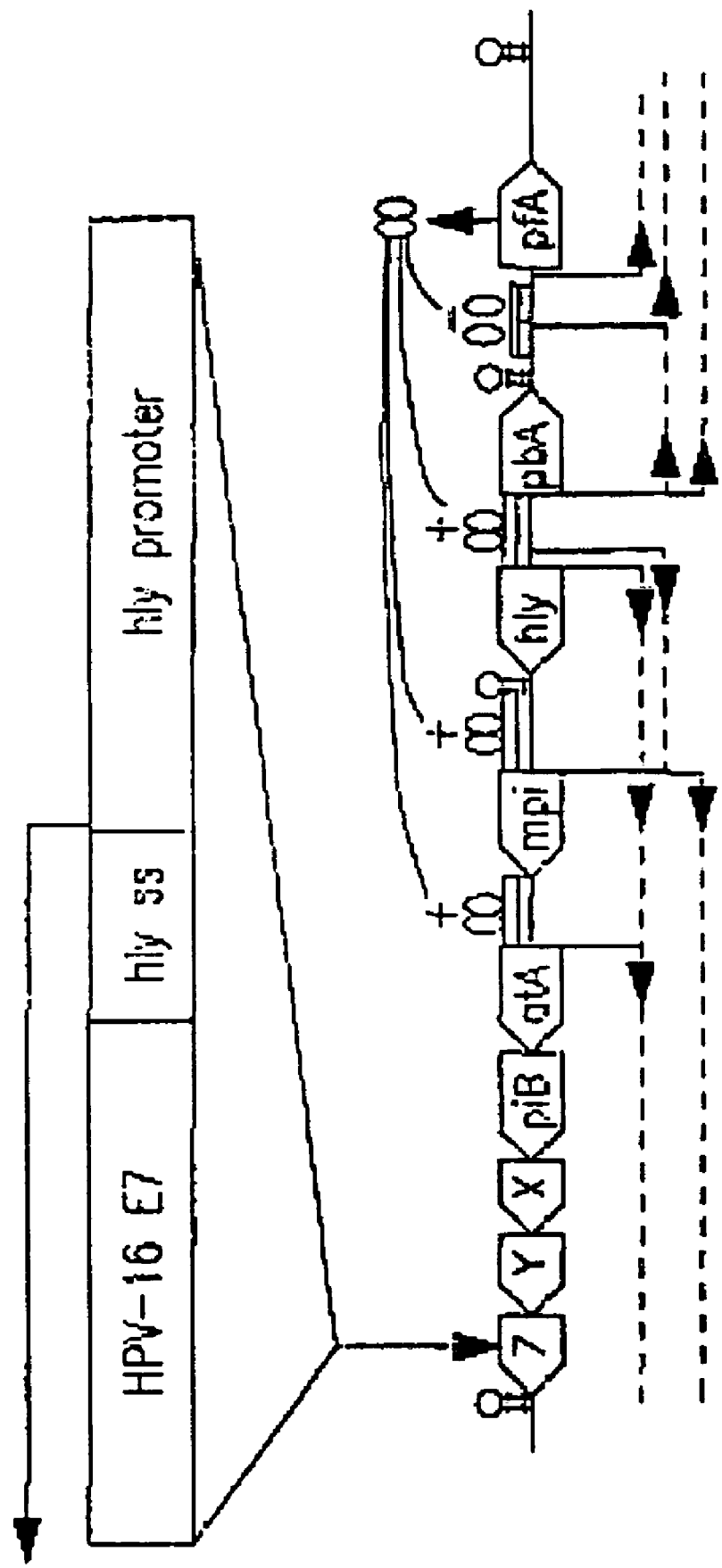
FIG. 1 is a diagram of an HPV-E7 chromosomal expression system constructed by integrating an E7 gene into the *Listeria* chromosome.

The present invention relates to a method for enhancing the immunogenicity of a selected antigen by fusion of the selected antigen to a non-hemolytic truncated form of listeriolysin O. It has now been found that fusion of an antigen to a non-hemolytic truncated form of listeriolysin O results in an antigen with enhanced immunogenicity as compared to an antigen alone. The truncated form of listeriolysin O fused to an antigen better enables cell mediated immunity and anti-tumor immunity as compared to antigen alone. Further, these fusion proteins need not be expressed by *L. monocytogenes*, but rather can be expressed and isolated from other vectors and cell systems routinely used for protein expression and isolation.

The present invention further comprises a recombinant *Listeria* vaccine strain including, inter alia, a fusion protein comprising an ActA protein, or fragment thereof, fused to an antigen. As demonstrated by the data disclosed herein, a recombinant *Listeria* vaccine strain comprising a fusion protein comprising ActA and an antigen, when administered to an animal, results in the destruction of existing tumors and the induction of antigen specific lymphocytes capable of infiltrating tumors and other diseases where a cellular immune response is beneficial. The present invention also encompasses a method for eliciting an enhanced immune response to an antigen by administering a composition comprising a *Listeria* vaccine strain comprising, inter alia, an antigen fused to an ActA protein, or fragment thereof. This is because, as demonstrated by the data disclosed herein, administering such a composition to an animal results in, among other things, a clearing of tumors, and the superior induction of lymphocytes specific for tumor antigens when compared to the administration of antigen that is not fused to an ActA protein, or fragment thereof. Further, the present invention comprises a method for enhancing the immunogenicity of an antigen. That is, as demonstrated by the data disclosed herein, fusing an ActA protein, or fragment thereof, to an antigen, results in, among other things, an improved clearance of tumors in animals and an enhanced antigen-specific immune response.

DEFINITIONS

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"ActA protein" is used herein to refer to the *Listeria monocytogenes* surface protein responsible for actin polymerization in infected cells. A "truncated ActA protein" is used herein to refer to an ActA protein missing one or more amino acids from the primary amino acid sequence of the native ActA protein. A "truncated ActA protein" comprises 390 amino acids (SEQ ID NO:23) encoded by 1170 nucleotides (SEQ ID NO:24).

"Antigen" is used herein to refer to a substance that when placed in contact with an organism, results in a detectable immune response. An antigen may be a lipid, peptide, protein, carbohydrate, nucleic acid, or combinations and variations thereof.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand.

By the term "applicator" as the term is used herein, is meant any device including, but not limited to, a hypodermic syringe, a pipette, and the like, for administering the proteins and *Listeria* strains of the invention to a mammal.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, adenoviruses, and adeno-associated viruses) that incorporate the recombinant polynucleotide.

A "fusion protein" as used herein refers to a protein wherein the protein comprises two or more proteins linked together by peptide bonds or other chemical bonds. The proteins can be linked together directly by a peptide or other chemical bond, or with one or more amino acids between the two or more proteins, referred to herein as a spacer.

"Fragment" is used herein to refer to a protein, peptide, or nucleic acid that is shorter or comprises fewer amino acids or nucleotides than the full length protein, peptide, or nucleic acid. By way of example, a fragment of a protein comprises less than the full length protein.

A "genomic DNA" is a DNA strand which has a nucleotide sequence homologous with a gene. By way of example, both a fragment of a chromosome and a cDNA derived by reverse transcription of a mammalian mRNA are genomic DNAs.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

In addition, when the terms "homology" or "identity" are used herein to refer to the nucleic acids and proteins, it should be construed to be applied to homology or identity at both the nucleic acid and the amino acid sequence levels.

As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals or organisms. This can be readily carried out by using hybridization probes to identify the same genetic locus in a variety of individuals or organisms. Any and all such nucleotide variations and resulting amino acid polymorphisms or variations that are the result of natural allelic variation and that do not alter the functional activity are intended to be within the scope of the invention.

"Immunogenicity" is used herein to refer to the innate ability of an antigen or organism to elicit an immune response in an animal when the antigen or organism is administered to the animal. Thus, "enhancing the immunogenicity" refers to increasing the ability of an antigen or organism to elicit an immune response in an animal when the antigen or organism is administered to an animal. The increased ability of an antigen or organism to elicit an immune response can be measured by, among other things, a greater number of antibodies to an antigen or organism, a greater diversity of antibodies to an antigen or organism, a greater number of T-cells specific for an antigen or organism, a greater cytotoxic or helper T-cell response to an antigen or organism, and the like.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "*Listeria* vaccine strain" is used herein to refer to a recombinant *Listeria* organism that expresses a heterologous antigen.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Transform", "transforming", and "transformation" is used herein to refer to a process of introducing an isolated nucleic acid into the interior of an organism.

Methods and Compositions

Listeriolysin O (LLO) binds to cholesterol-containing membranes wherein it oligomerizes to form pores. The oligomerization is dependent on the presence of a reduced cystine residue at position 484 in the sequence that is required for oligomerization. The hly gene encodes a proprotein of 529 residues (GenBank Accession No. P13128), the first 25 amino acids are the signal sequence and are cleaved from LLO when it is secreted by the bacterium. Thus, the full length active LLO protein is approximately 504 residues. For purposes of the present invention, by "truncated LLO or ΔLLO" it is meant a fragment of LLO which does not contain the activation domain at the amino terminus and does not include cystine 484.

The present invention also relates to methods and compositions for enhancing cell mediated or anti-tumor immunity of a selected antigen by fusion of the selected antigen to a PEST-like amino acid sequence derived from a prokaryotic organism. For purposes of the present invention, by "PEST-like amino acid sequence" it is meant a peptide rich in the amino acids proline (P), glutamic acid (E), serine (S) and threonine (T). In a preferred embodiment the PEST-like amino acid sequence is derived from the amino acid terminus of Listeriolysin O (LLO), a hemolytic virulence factor of $L.$ $monocytogenes$. In a more preferred embodiment, the PEST-like amino acid sequence comprises KENSISSMAPPASP-PASPKTPIEKKHADEIDK (SEQ ID NO:1).

Enhanced cell mediated immunity was demonstrated for fusion proteins comprising an antigen and truncated LLO containing the PEST-like amino acid sequence, SEQ ID NO: 1. The ΔLLO used in these experiments was 416 amino acids long as 88 residues from the amino terminus which is inclusive of the activation domain containing cystine 484 were truncated. However, it is believed that other ΔLLOs without the activation domain, and in particular cystine 484, will also be effective. More particularly, it is believed that fusion of an antigen to any ΔLLO including the PEST-like amino acid sequence, SEQ ID NO: 1, can enhance cell mediated and anti-tumor immunity of the antigen.

Enhanced immunogenicity of an antigen following fusion to a non-hemolytic truncated form of listeriolysin O was demonstrated. Specifically, experiments have been performed demonstrating that an $L. monocytogenes$ vector that expresses and secretes a fusion product of Human Papilloma Virus (HPV) strain 16 E7 and listeriolysin, which comprises the PEST-like amino acid sequence SEQ ID NO:1, is a much more potent cancer immunotherapeutic for HPV immortalized tumors than a strain of $L. monocytogenes$ that secretes the E7 protein alone. Experiments were also performed demonstrating that a recombinant vaccinia virus that carries the gene for the fusion protein LLO-E7 which contains the PEST-like amino acid sequence of SEQ ID NO:1 is a much more potent cancer immunotherapeutic for HPV immortalized tumors than an isogenic strain of vaccinia that carries the gene for E7 protein alone. In comparison, a short fusion protein Lm-AZ/-E7 comprising the E7 antigen fused to the promoter, signal sequence and the first 7 amino acid residues of LLO was an ineffective anti-tumor immunotherapeutic. This short fusion protein terminates directly before the PEST-like sequence and does not contain it.

The present invention comprises an antigen fused to a truncated ActA protein, or fragment thereof. This is because, as demonstrated by the data disclosed herein, an antigen fused to a truncated ActA protein, or fragment thereof, when administered to an animal results in, among other things, clearing of existing tumors, and the induction of antigen specific CD8$^+$ cells capable of infiltrating infected or tumor cells. Therefore, as demonstrated by the data disclosed herein, ActA has the function or activity of enhancing the immunogenicity of an antigen. Thus the present invention includes a fusion protein comprising an antigen fused to a truncated ActA protein, or fragment thereof. Fusion proteins comprising an antigen may be prepared by any suitable method, including, for example, cloning and restriction of appropriate sequences or direct chemical synthesis by methods discussed below. Alternatively, subsequences may be cloned and the appropriate subsequences cleaved using appropriate restriction enzymes. The fragments may then be ligated to produce the desired DNA sequence. Preferably, DNA encoding the antigen can be produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The antigen can then be ligated into a plasmid.

The truncated ActA protein, or fragment thereof, and the antigen can be conjugated by any of a number of means well known to those of skill in the art. Typically the antigen is conjugated, either directly or through a linker (spacer), to the ActA protein. However, where both the antigen and the ActA protein are polypeptides it is preferable to recombinantly express the chimeric molecule as a single-chain fusion protein.

Where the ActA protein and/or the antigen is relatively short (i.e., less than about 50 amino acids) they may be synthesized using standard chemical peptide synthesis techniques. Where both molecules are relatively short the chimeric molecule may be synthesized as a single contiguous polypeptide. Alternatively the ActA protein and the antigen may be synthesized separately and then fused by condensation of the amino terminus of one molecule with the carboxyl terminus of the other molecule thereby forming a peptide bond. Alternatively, the ActA protein and antigen can each be condensed with one end of a peptide spacer molecule thereby forming a contiguous fusion protein.

The peptides and proteins (i.e. truncated ActA and an antigen) of the present invention may be readily prepared by standard, well-established solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky (The Practice of Peptide Synthesis, 1984, Springer-Verlag, New York). At the outset, a suitably protected amino acid residue is attached through its carboxyl group to a derivatized, insoluble polymeric support, such as cross-linked polystyrene or polyamide resin. "Suitably protected" refers to the presence of protecting groups on both the alpha-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method which utilized tert-butyloxycarbonyl as the alpha-amino protecting group, and the FMOC method which utilizes 9-fluorenylmethyloxycarbonyl to protect the alpha-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dichloromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequencers, which sequentially degrade the peptide and identify the amino acids in order, may also be used to determine definitely the sequence of the peptide.

Prior to its use, the peptide is purified to remove contaminants. In this regard, it will be appreciated that the peptide will be purified so as to meet the standards set out by the appropriate regulatory agencies and guidelines. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield in Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963), and Stewart et al., Solid Phase Peptide Synthesis, 2nd ed. Pierce Chem. Co., Rockford, Ill. (1984).

Further, the chimeric fusion proteins of the present invention can be synthesized using recombinant DNA methodology. Generally this involves creating a DNA sequence that encodes the fusion protein, placing the DNA in an expression cassette, such as the plasmid of the present invention, under the control of a particular promoter/regulatory element, and expressing the protein.

DNA encoding the fusion protein (e.g. truncated ActA/ antigen) of the present invention may be prepared by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al. (1981, Tetra. Lett., 22: 1859-1862); and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill in the art would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

The present invention includes an isolated nucleic acid encoding a truncated ActA molecule, or a fragment thereof, fused to an antigen, wherein the nucleic acid is at least about 80% homologous, more preferably at least about 90% homologous with a nucleic acid having the sequence of SEQ ID NO:24. Preferably, the nucleic acid is at least about 95% homologous, more preferably at least about 96% homologous with a nucleic acid having the sequence of SEQ ID NO:24, more preferably at least about 97% homologous with a nucleic acid having the sequence of SEQ ID NO:24, more preferably at least about 98% homologous with a nucleic acid having the sequence of SEQ ID NO:24, more preferably at least about 99% homologous with a nucleic acid having the sequence of SEQ ID NO:24, most preferably, about 99.9% homologous to SEQ ID NO:24, disclosed herein. Even more preferably, the nucleic acid is SEQ ID NO:24. The isolated nucleic acid of the invention should be construed to include an RNA or a DNA sequence encoding an ActA protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Such modifications are detailed elsewhere herein. Any and all combinations of modifications of the nucleotide sequences are contemplated in the present invention.

In other related aspects, the invention includes an isolated nucleic acid encoding a truncated ActA protein and an isolated nucleic acid encoding an antigen operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

Expression of a truncated ActA protein and an antigen, either alone or fused to a detectable tag polypeptide in a cell or mammal may be accomplished by generating a plasmid, viral, or other type of vector comprising the desired nucleic acid operably linked to a promoter/regulatory sequence which serves to drive expression of the protein, with or without tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, both of which were used in the experiments disclosed herein, as well as the Rous sarcoma virus promoter, and the like. Moreover, inducible and tissue specific expression of the nucleic acid encoding a truncated ActA protein and an antigen may be accomplished by placing the nucleic acid encoding a truncated ActA protein and an antigen, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Expressing a truncated ActA protein and an antigen using a vector allows the isolation of large amounts of recombinantly produced protein. Selection of any particular plasmid vector or other DNA vector is not a limiting factor in this invention and a wide plethora of vectors are well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The invention thus includes a vector comprising an isolated nucleic acid encoding a truncated ActA protein and an antigen. The incorporation of a desired nucleic acid into a vector and the choice of vectors is well-known in the art as described in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The invention also includes cells, viruses, proviruses, and the like, containing such vectors. Methods for producing cells comprising vectors and/or exogenous nucleic acids are well-known in the art. See, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The nucleic acids encoding a truncated ActA protein and an antigen may be cloned into various plasmid vectors. However, the present invention should not be construed to be limited to plasmids or to any particular vector. Instead, the present invention should be construed to encompass a wide plethora of vectors which are readily available and/or well-known in the art.

The present invention further includes a truncated ActA polypeptide, or a fragment thereof, fused to an antigen, wherein the polypeptide is at least about 80% homologous, more preferably at least about 90% homologous with a polypeptide sequence having the sequence of SEQ ID NO:23. Preferably, the polypeptide is at least about 95% homologous, more preferably at least about 96% homologous with a polypeptide having the sequence of SEQ ID NO:23, more preferably at least about 97% homologous with a polypeptide having the sequence of SEQ ID NO:23, more preferably at least about 98% homologous with a polypeptide having the sequence of SEQ ID NO:23, more preferably at least about 99% homologous with a polypeptide having the sequence of SEQ ID NO:23, most preferably, about 99.9% homologous to SEQ ID NO:23, disclosed herein. Even more preferably, the polypeptide is SEQ ID NO:23.

The present invention should not be construed as being limited solely to the nucleic and amino acid sequences disclosed herein. Once armed with the present invention, it is readily apparent to one skilled in the art that other nucleic acids encoding an ActA protein fused to an antigen can be obtained by following the procedures described herein in the experimental details section for the generation of other ActA/ antigen fusion proteins as disclosed herein (e.g., site-directed mutagenesis, frame shift mutations, and the like), and procedures that are well-known in the art or to be developed.

Further, any other number of procedures may be used for the generation of derivative or variant forms of an ActA/ antigen fusion protein using recombinant DNA methodology well known in the art such as, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York), and elsewhere herein.

Procedures for the introduction of amino acid changes in a protein or polypeptide by altering the DNA sequence encoding the polypeptide are well known in the art and are also described in Sambrook et al. (1989, supra); Ausubel et al. (1997, supra).

The invention includes a nucleic acid encoding an ActA/ antigen fusion protein wherein a nucleic acid encoding a tag polypeptide is covalently linked thereto. That is, the invention encompasses a chimeric nucleic acid wherein the nucleic acid sequence encoding a tag polypeptide is covalently linked to the nucleic acid encoding an ActA/antigen fusion protein. Such tag polypeptides are well known in the art and include, for instance, green fluorescent protein (GFP), myc, myc-pyruvate kinase (myc-PK), $His_6$, maltose biding protein (MBP), an influenza virus hemagglutinin tag polypeptide, a flag tag polypeptide (FLAG), and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

The nucleic acid comprising a nucleic acid encoding a tag polypeptide can be used to localize an ActA/antigen fusion protein within a cell, a tissue, and/or a whole organism (e.g., a mammalian embryo), detect an ActA/antigen fusion protein secreted from a cell, and to study the role(s) of an ActA/ antigen fusion protein in a cell. Further, addition of a tag polypeptide facilitates isolation and purification of the "tagged" protein such that the proteins of the invention can be produced and purified readily.

As an example, DNA encoding the fusion protein of the present invention may be cloned using DNA amplification methods such as polymerase chain reaction (PCR). Thus, the gene for truncated ActA is PCR amplified, using a sense primer comprising a suitable restriction site and an antisense primer comprising another restriction site, preferably a non-identical restriction site to facilitate cloning. The same is repeated for the isolated nucleic acid encoding an antigen. Ligation of the truncated ActA and antigen sequences and insertion into a plasmid or vector produces a vector encoding truncated ActA joined to a terminus of the antigen. The two molecules are joined either directly or by a short spacer introduced by the restriction site.

While the two molecules are preferably essentially directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The present invention comprises a truncated ActA protein, or fragment thereof, fused to an antigen. Methods for the fusion of an antigen to an ActA protein are disclosed elsewhere herein. The truncated ActA protein, or fragment thereof, of the present invention comprises the ActA amino acid sequence set forth in SEQ ID NO:23. The skilled artisan will recognize that the ActA protein of the present invention need not be that which is set forth exactly in SEQ ID NO:23, but rather that other alterations, modifications, or changes can be made that retain the functional characteristics of an ActA protein fused to an antigen as set forth elsewhere herein.

It will be appreciated, of course, that the peptides may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkyl amino groups such as methyl amino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for analogs of truncated ActA, or fragments thereof, proteins or peptides. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention further comprises an antigen with enhanced immunogenicity. That is, as the data disclosed herein demonstrate, an antigen fused to a truncated ActA protein, or fragment thereof, when administered to an animal, results in a clearance of existing tumors and the induction of antigen specific cytotoxic lymphocytes capable of infiltrating tumor or infected cells. When armed with the present disclosure, and the methods and compositions disclosed herein, the skilled artisan will readily realize that the present invention in amenable to treatment and/or prevention of a multitude of diseases.

The antigen fused to the truncated ActA protein, or fragment thereof is preferably an antigen derived from a tumor or an infectious organism, including, but not limited to fungal pathogens, bacteria, parasites, helminths, viruses, and the like. An antigen comprising the fusion protein of the present invention includes but is not limited to, tetanus toxoid, hemagglutinin molecules from influenza virus, diphtheria toxoid, HIV gp120, HIV gag protein, IgA protease, insulin peptide B, *Spongospora subterranea* antigen, vibriose antigens, *Salmonella* antigens, pneumococcus antigens, respiratory syncytial virus antigens, *Haemophilus influenza* outer membrane proteins, *Helicobacter pylori* urease, *Neisseria meningitidis* pilins, *N. gonorrhoeae* pilins, the melanoma-associated antigens (TRP-2, MAGE-1, MAGE-3, gp-100, tyrosinase, MART-1, HSP-70, beta-HCG), human papilloma virus antigens E1, E2, E6 and E7 from type HPV-16, -18, -31, -33, -35 or -45 human papilloma viruses, the tumor antigens CEA, the ras protein, mutated or otherwise, the p53 protein, mutated or otherwise, Muc1, pSA, the antigens well known in the art from the following diseases; cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough, yellow fever, the immunogens and antigens from Addison's disease, allergies, anaphylaxis, Bruton's syndrome, cancer, including solid and blood borne tumors, eczema, Hashimoto's thyroiditis, polymyositis, dermatomyositis, type I diabetes mellitus, acquired immune deficiency syndrome, transplant rejection, such as kidney, heart, pancreas, lung, bone, and liver transplants, Graves' disease, polyendocrine autoimmune disease, hepatitis, microscopic polyarteritis, polyarteritis nodosa, pemphigus, primary biliary cirrhosis, pernicious anemia, coeliac disease, antibody-mediated nephritis, glomerulonephritis, rheumatic diseases, systemic lupus erthematosus, rheumatoid arthritis, seronegative spondylarthritides, rhinitis, sjogren's syndrome, systemic sclerosis, sclerosing cholangitis, Wegener's granulomatosis, dermatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, non-Hodgkin's lymphoma, malarial circumsporozite protein, microbial antigens, viral antigens, autoantigens, and lesteriosis.

Tumor antigens contemplated in the present invention include, but are not limited to, any of the various MAGEs (Melanoma-Associated Antigen E), including MAGE 1 (e.g., GenBank Accession No. M77481), MAGE 2 (e.g., GenBank Accession No. U03735), MAGE 3, MAGE 4, etc.; any of the various tyrosinases; mutant ras; mutant p53 (e.g., GenBank Accession No. X54156 and AA494311); and p97 melanoma antigen (e.g., GenBank Accession No. M12154). Other tumor-specific antigens include the Ras peptide and p53 peptide associated with advanced cancers, the HPV 16/18 and E6/E7 antigens associated with cervical cancers, MUC1-KLH antigen associated with breast carcinoma (e.g., GenBank Accession No. J03651), CEA (carcinoembryonic antigen) associated with colorectal cancer (e.g., GenBank Accession No. X98311), gp100 (e.g., GenBank Accession No. S73003) or MART1 antigens associated with melanoma, and the PSA antigen associated with prostate cancer (e.g., GenBank Accession No. X14810). The p53 gene sequence is known (See e.g., Harris et al. (1986) Mol. Cell. Biol., 6:4650-4656) and is deposited with GenBank under Accession No. M14694. Tumor antigens encompassed by the present invention further include, but are not limited to, Her-2/Neu (e.g. GenBank Accession Nos. M16789.1, M16790.1, M16791.1, M16792.1), NY-ESO-1 (e.g. GenBank Accession No. U87459), hTERT (aka telomerase) (GenBank Accession. Nos. NM003219 (variant 1), NM198255 (variant 2), NM 198253 (variant 3), and NM 198254 (variant 4), proteinase 3 (e.g. GenBank Accession Nos. M29142, M75154, M96839, X55668, NM 00277, M96628 and X56606) HPV E6 and E7 (e.g. GenBank Accession No. NC 001526) and WT-1 (e.g. GenBank Accession Nos. NM000378 (variant A), NM024424 (variant B), NM 024425 (variant C), and NM024426 (variant D)). Thus, the present invention can be used as immunotherapeutics for cancers including, but not limited to, cervical, breast, colorectal, prostate, lung cancers, and for melanomas.

The present invention further includes, but is not limited to the antigens from the following infectious diseases; measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Japanese encephalitis (e.g., GenBank Accession No. E07883), dengue (e.g., GenBank Accession No. M24444), hantavirus, and HIV (e.g., GenBank Accession No. U18552). Bacterial and parasitic antigens will be derived from known causative agents responsible for diseases including, but not limited to, diphtheria, pertussis (e.g., GenBank Accession No. M35274), tetanus (e.g., GenBank Accession No. M64353), tuberculosis, bacterial and fungal pneumonias (e.g., *Haemophilus influenzae, Pneumocystis carinii*, etc.), cholera, typhoid, plague, shigellosis, salmonellosis (e.g., GenBank Accession No. L03833), Legionnaire's Disease, Lyme disease (e.g., GenBank Accession No. U59487), malaria (e.g., GenBank Accession No. X53832), hookworm, onchocerciasis (e.g., GenBank Accession No. M27807), schistosomiasis (e.g., GenBank Accession No. L08198), trypanosomiasis, leshmaniasis, giardiasis (e.g., GenBank Accession No. M33641), amoebiasis, filariasis (e.g., GenBank Accession No. J03266), borreliosis, and trichinosis.

The antigens of these and other diseases are well known in the art, and the skilled artisan, when equipped with the present disclosure and the methods and techniques described herein will readily be able to construct a fusion protein comprising a truncated ActA protein and an antigen for use in the present invention.

The skilled artisan, when armed with the present disclosure and the data herein, will readily appreciate that a truncated ActA protein, or fragments thereof, can be fused to the antigens enumerated herein, and others well known in the art. While not wishing to be bound by any particular theory, the data disclosed herein demonstrate that an antigen fused to an ActA protein, or fragment thereof, is processed in the cellular cytoplasm and presented in the context of the major histocompatability complex to effector lymphocytes. Therefore, as is well known by those having knowledge of the fundamental tenets of immunology, an antigen fused to an ActA protein, or fragment thereof, will be degraded through well-known cellular pathways and be displayed on the cell surface for recognition by effector and helper lymphocytes. As is well known in the art, the degradation process results in short peptide sequences presented in the context of the major histocompatability complex that are subsequently recognized by T-cells, resulting in effector or helper functions. Thus, the secondary, tertiary and quaternary structures of the antigen fused to a truncated ActA protein, or fragment thereof are not necessarily material to the present invention. However the primary amino acid sequence of the antigen is material to the methods and compositions presented herein. As demonstrated by the data disclosed herein, the antigen is recognized by lymphocytes according to short T cell epitopes, the structure of which is not modified, altered, or otherwise changed by fusion to another protein. Thus, while the present invention is described in reference to certain antigens, the skilled artisan will readily appreciate that the present invention is amendable to any antigen disclosed herein or otherwise well known in the art.

In a first set of experiments, the HPV-E7 antigen was expressed in *L. monocytogenes*. An *L. monocytogenes* recombinant that expressed E7 was made by chromosomal integration of the E7 gene under the control of the hly promoter and with the inclusion of the hly signal sequence to ensure secretion of the gene product. The site of integration into the chromosome by homologous recombination was into a region that is non-essential for Lm virulence. The scheme for this is depicted in FIG. 1. The expression and secretion of the antigen from the resulting recombinants, Lm-E7, was verified by Western Blot. In addition, therapeutic effects of Lm-E7 were optimized. For example, it was found that the best results were achieved delivering the vaccine orally as compared to parenterally and in a combined protection and regression mode that requires priming with Lm-E7 before tumor challenge and then administering Lm-E7 therapeutically after tumor challenge. Table 1 provides more details for optimized anti-tumor effects observed in this model in three different tumor cell lines, TC-1, C3 and EL-4/E7. Bacteria were delivered orally 14 and 7 days prior to tumor challenge and days 7 and 14 following tumor challenge. Delivery of $10^6$ bacteria intraperitoneally in a similar protocol provided no long-term protection. However, better protection was observed when Lm-E7 was delivered orally. More specifically, with this regimen approximately 50% of the animals remained tumor free in perpetuity and immunization seriously retarded tumor growth in all animals.

TABLE 1

Treatment with Lm-E7

| | Number of tumor free animals versus total in study (number survived) | | |
|---|---|---|---|
| Treatment | $10^5$ TC-1 on Day 60 | $10^6$ C3 on Day 42 | $5 \times 10^5$ EL-4/E7, Day 40 |
| $10^8$ Lm-E7 | 3/8 (5) | 4/8 (8) | 4/8 (6) |
| $10^8$ Lm-Gag (ZY-18) | 2/8 (2) | 0/8 (0) | 2/8 (0) |
| Naive | 0/8 (0) | 0/8 (0) | 1/8 (0) |

Animals administered TC-1 or EL-4/E7 tumor cells that were tumor free were re-challenged on day 60 with TC-1 or day 40 EL-4/E7, respectively. The two animals in each group that had been immunized with Lm-Gag grew tumors whereas the animals immunized with Lm-E7 remained tumor free until termination of the experiment (day 124 in the case of TC-1 and day 54 for EL-4/E7).

Compared to results previously disclosed with Lm-NP and the RENCA, CT-26 and B16F10-NP models (Pan et al., 1995, Cancer Res. 55:4776-4779), the Lm-E7 was less effective than expected. Accordingly, an Lm-E7 construct was prepared in accordance with the method taught for preparation of the Lm-NP construct of Pan et al. (Pan et al., 1995, Cancer Res. 1995 55:4776-4779).

Figure 2:
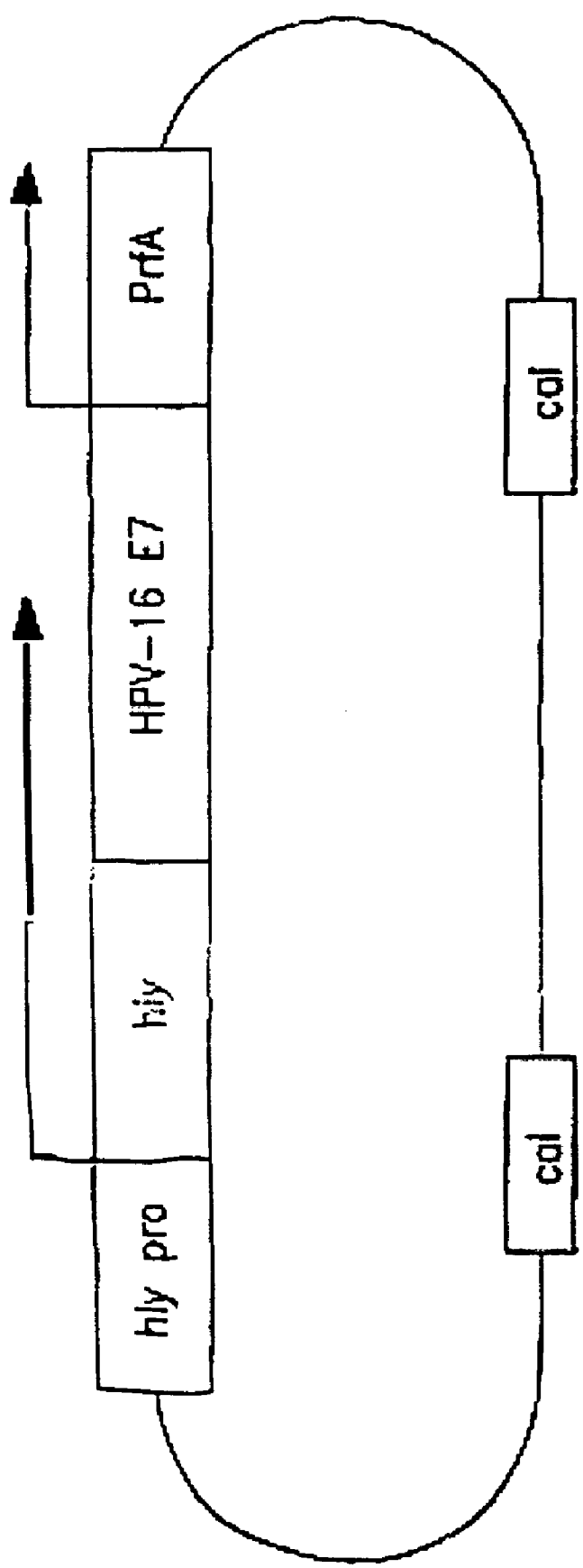
FIG. 2 is a diagram of a preferred multi-copy plasmid containing prfA and E7 fused to a truncated form of the hly gene (Δhly) that produced ΔLLO.

Specifically, a second *L. monocytogenes* vaccine that expresses a E7 fusion protein, referred to as Lm-LLO-E7, was prepared by complementing a prfA-deletion mutant with a plasmid containing a copy of the prfA gene and a copy of the E7 gene fused to a form of the hly gene truncated to eliminate the hemolytic activity of the enzyme, ΔLLO (see FIG. 2). Functional LLO is maintained by the organism via the endogenous chromosomal copy of hly. The expression and secretion of the fusion protein was verified by Western blot.

The ability of the Lm-LLO-E7 and Lm-E7 vaccine to induce anti-tumor immunity was then compared in a regression model. As shown in Table 2, Lm-LLO-E7 was found to be more effective than Lm-E7. This difference in efficacy is believed to be due to the presence of the PEST-like sequence, SEQ ID NO:1, in Lm-LLO-E7.

TABLE 2

Number of mice cured of TC-1 tumor at conclusion of experiment

| Treatment | Mice TC-1 free at Day 45 | Mice alive at day 45 | Mice alive at day 134 |
|---|---|---|---|
| Naive | 0/8 | 0/8 | 0/8 |
| Lm-LLO-E7 | 4/8 | 8/8 | 4/8 |
| Lm-E7 | 0/8 | 7/8 | 0/8 |

Thus, expression of the foreign gene as a fusion protein with ΔLLO enhances the immunogenicity of the antigen.

Figure 3:
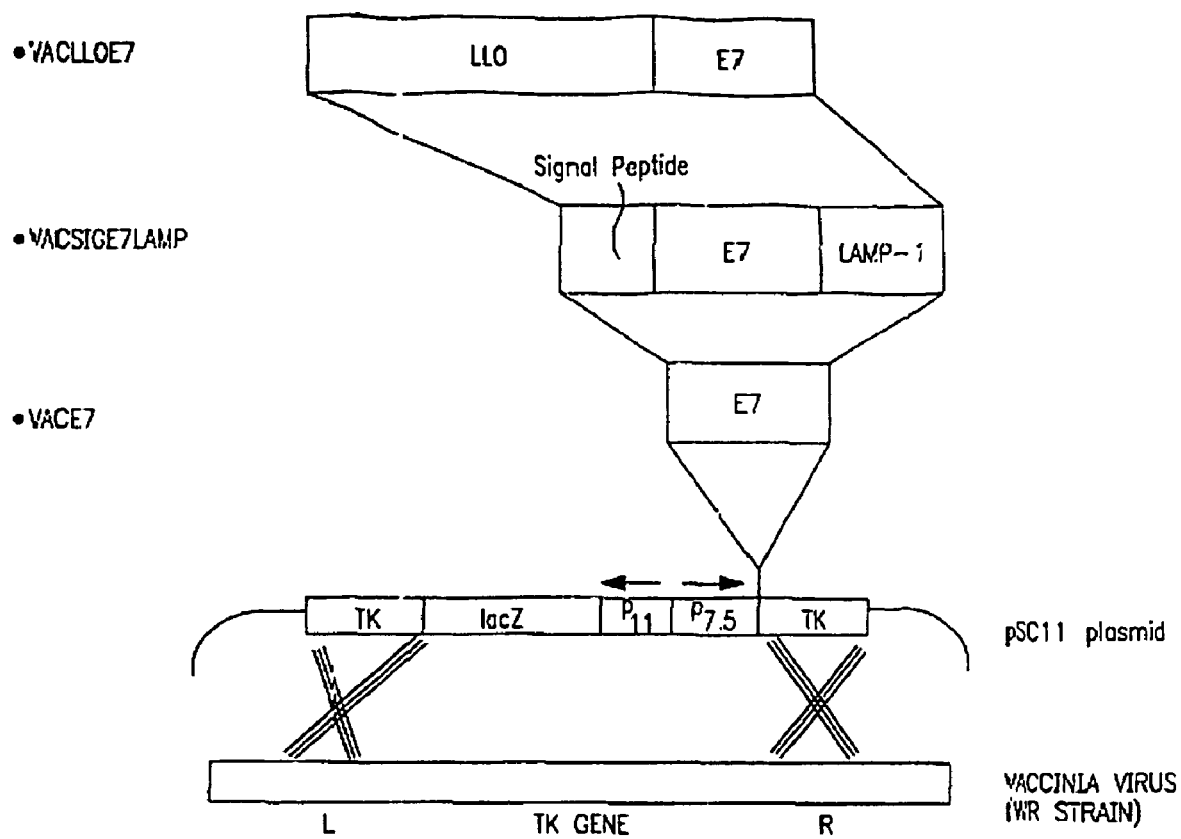
FIG. 3 is a graph showing tumor immunotherapeutic efficacy of E7 antigen expressed in *L. monocytogenes*. Tumor size in millimeters in mice is shown at 7, 14, 21, 28 and 56 days post tumor-inoculation. Naive mice are depicted by an open-circle; mice administered Lm-LLO-E7 are depicted by a filled circle; mice administered Lm-E7 are depicted by a square; mice administered Lm-Gag are depicted by an open diamond; and mice administered Lm-LLO-NP are depicted by a filled triangle.
Figure 4:
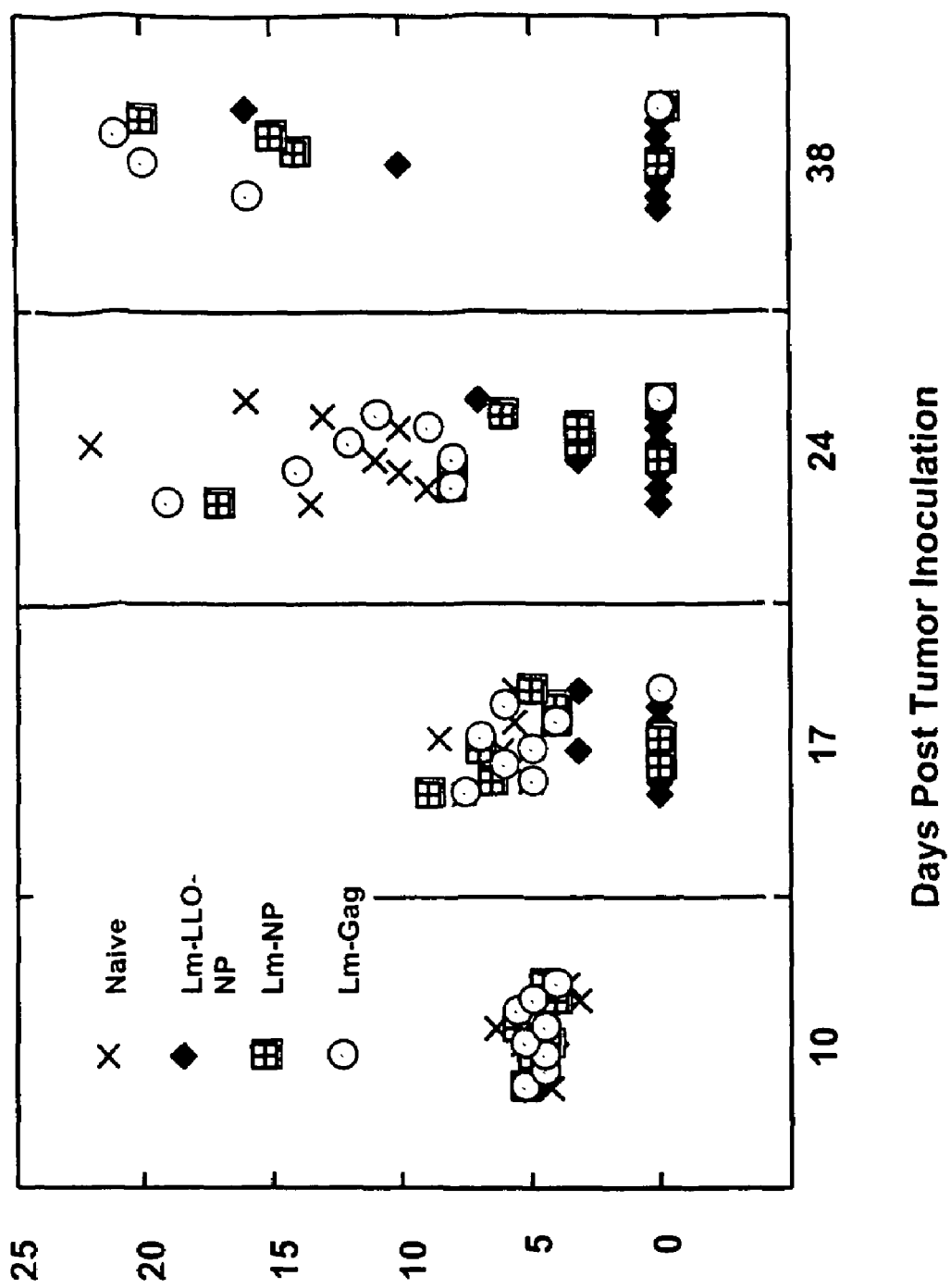
FIG. 4 is a graph showing tumor immunotherapeutic efficacy of NP antigen expressed in *L. monocytogenes*. Tumor size in millimeters in mice is shown at 10, 17, 24, and 38 days post tumor-inoculation. Naive mice are depicted by an X; mice administered Lm-LLO-NP are depicted by a filled diamond; mice administered Lm-NP are depicted by a square; and mice administered Lm-Gag are depicted by an open circle.

Additional experiments were performed to compare the ability of Lm-E7 with Lm-LLO-E7 to induce the regression of established sub-cutaneous HPV-16 immortalized tumors from C57Bl/6 mice. Results from these experiments are depicted in FIG. 3. In these experiments, mice were immunized i.p. with 0.1 $LD^{50}$ with one of four constructs, Lm-E7, Lm-Gag (isogenic with Lm-E7 except for the antigen expressed), Lm-LLO-E7 or Lm-LLO-NP. Lm-LLO-NP is isogenic with Lm-LLO-E7 but expresses influenza antigen. A second immunization was performed on day 14. As can be seen in FIG. 3, 6 of 8 mice immunized with Lm-LLO-E7 were cured of their tumors and remained tumor free. None of the other animals demonstrated any regression of the established tumors. Similar results have been achieved for Lm-LLO-E7 under different immunization protocols. Further, just one immunization has been demonstrated to cure mice of established TC-1 of 5 mm diameter. In order to confirm the generality of the finding that fusing LLO to an antigen confers enhanced immunity, a version of Lm-NP similar to Lm-E7 was constructed. This recombinant was prepared as depicted in FIG. 1 except that influenza nucleoprotein replaced E7 as the antigen. The ability of the new Lm-NP was compared with Lm-LLO-NP (described in U.S. Pat. No. 5,830,702 and prepared as depicted in FIG. 2). Results from these experiments are depicted in FIG. 4. In these experiments, 32 BALB/c mice were inoculated with $5 \times 10^5$ RENCA-NP tumor cells. RENCA-NP is a renal cell carcinoma retrovirally transduced with influenza nucleoprotein NP (described in U.S. Pat. No. 5,830,702). After palpable macroscopic tumors had grown on day 10, eight animals in each group were immunized i.p. with 0.1 $LD_{50}$ with one of three constructs, Lm-NP, Lm-Gag (isogenic with Lm-NP except for the antigen expressed) and Lm-LLO-NP. The animals received a second immunization one week later. Eight animals were left untreated. At the end of the experiment on day 40, all the mice in the naive group had large tumors or had died. Only one mouse in the group that received Lm-Gag and two mice in the group that received Lm-NP were tumor free. This experiment demonstrates that fusing an antigen to LLO is not restricted to E7 and suggests that the form of the antigen is not important.

Additional experiments were performed to confirm the enhanced therapeutic efficacy of a fusion protein comprising the E7 antigen and a truncated form of listeriolysin O. In these experiments a vaccinia vector that expresses E7 as a fusion protein with a non-hemolytic truncated form of listeriolysin O was constructed. The WR strain of vaccinia was used as the recipient and the fusion gene was excised from the listerial plasmid and inserted into pSC11 under the control of the p75 promoter. This vector was chosen because it is the transfer vector used for the vaccinia constructs Vac-SigE7Lamp and Vac-E7 and would therefore allow direct comparison with Vac-LLO-E7. In this way all three vaccinia recombinants would be expressed under control of the same early/late compound promoter p7.5. In addition SC11 allows the selection of recombinant viral plaques to TK selection and beta-galactosidase screening.

Figure 5:
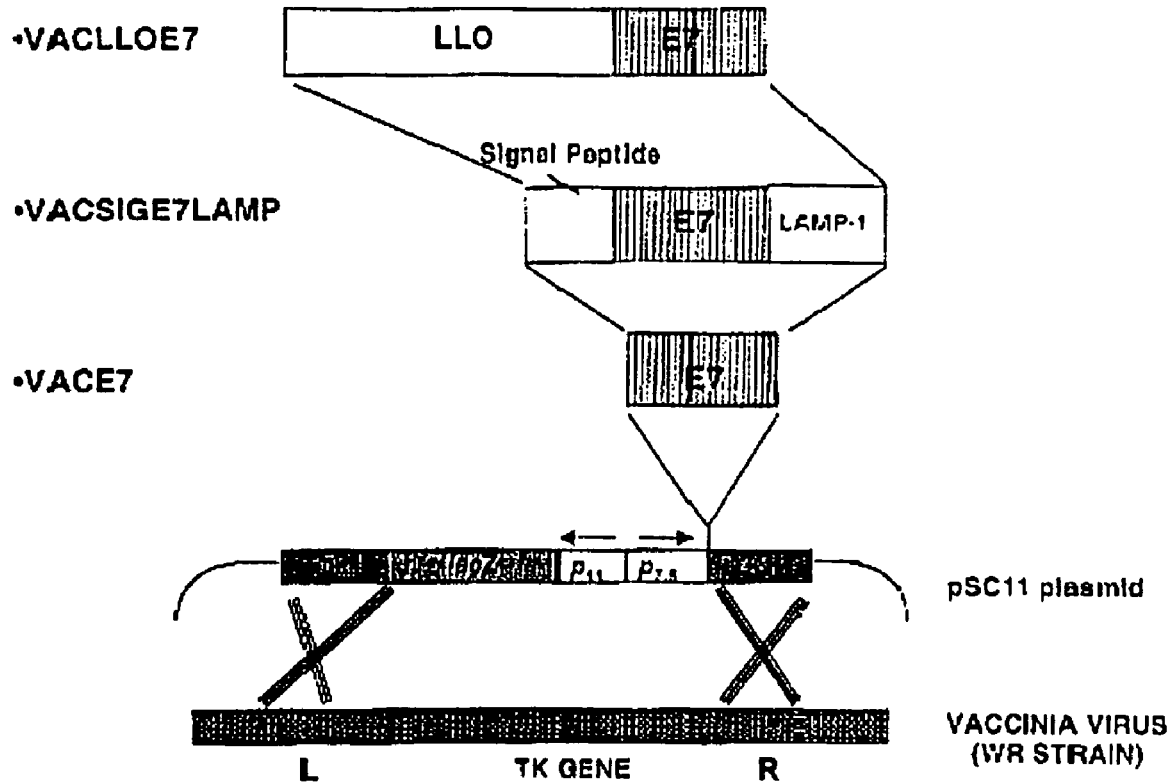
FIG. 5 is a diagram of various Vaccinia virus constructs expressing different forms of HPV16 E7 protein.

FIG. 5 depicts the various vaccinia constructs used in these experiments. Vac-SigE7Lamp is a recombinant vaccinia virus that expressed the E7 protein fused between lysosomal associated membrane protein (LAMP-1) signal sequence and sequence from the cytoplasmic tail of LAMP-1 (Lin et al. Proc. Natl. Acad. Sci. USA 1995 92:11671-5; Wu et al. Cancer Res. 1996 56:21-6). It was designed to facilitate the targeting of the antigen to the MHC class II pathway.

The following modifications were made to allow expression of the gene product by vaccinia: (a) the T5XT sequence that prevents early transcription by vaccinia was removed from the 5' portion of the LLO-E7 sequence by PCR; and (b) an additional XmaI restriction site was introduced by PCR to allow the final insertion of LLO-E7 into SC11. Successful introduction of these changes (without loss of the original sequence that encodes for LLO-E7) was verified by sequencing. The resultant pSC11-E7 construct was used to transfect the TK-ve cell line CV1 that had been infected with the wildtype vaccinia strain, WR. Cell lysates obtained from this co-infection/transfection step contain vaccinia recombinants that were plaque purified 3 times. Expression of the LLO-E7 fusion product by plaque purified vaccinia was verified by Western blot using an antibody directed against the LLO protein sequence. In addition, the ability of Vac-LLO-E7 to produce CD8+ T cells specific to LLO and E7 was determined using the LLO (91-99) and E7 (49-57) epitopes of Balb/c and C57/BL6 mice, respectively. Results were confirmed in a chromium release assay.

Figure 6:
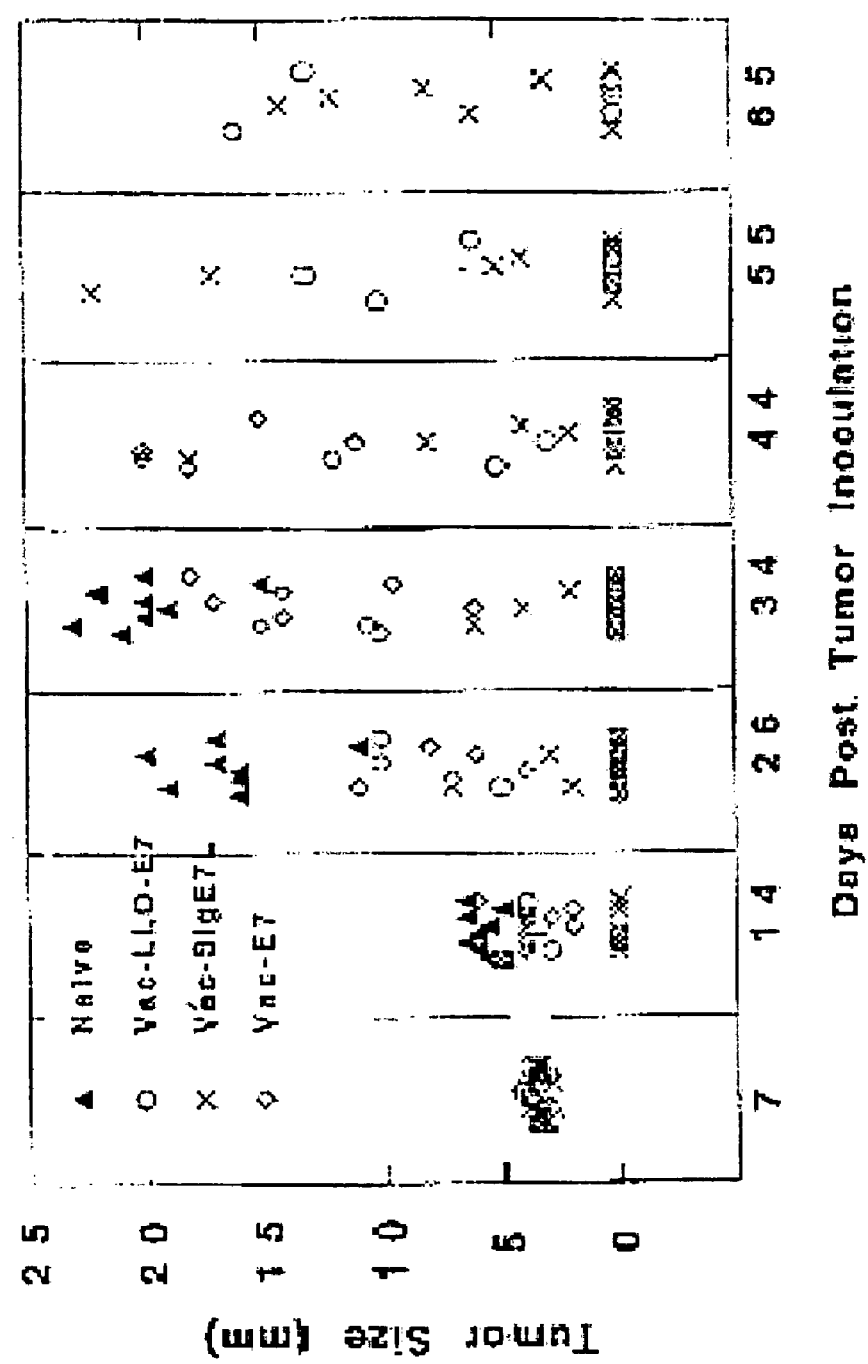
FIG. 6 is a graph showing tumor immunotherapeutic efficacy of antigens expressed by Vaccinia. Tumor size in millimeters in mice is shown at 7, 14, 26, 34, 44, 55 and 65 days post tumor-inoculation. Naive mice are depicted by a filled triangle; mice administered Vac-LLO-E7 are depicted by an open circle; mice administered Vac-SigE7L are depicted by an X; and mice administered Vac-E7 are depicted by an open diamond.

Tumor rejection studies were performed with TC-1 following the same protocol as described herein. Two experiments were performed with differing delays before treatment was started. In one experiment, treatments were initiated when the tumors were about 3 mm in diameter (see FIG. 6). As of day 76, 50% of the Vac-LLO-E7 treated mice are tumor free and 25% of the Vac-SigE7Lamp mice are tumor free.

In a second experiment, TC-1 tumors were grown to a larger size (5 to 6 mm). The LLO-E7 fusion protein based vectors were then compared against a larger number of vectors. Although some of the vaccine groups showed significant temporary regression of TC-1, by day 65 the data demonstrates that Lm-LLO-E7 and Vac-LLO-E7 were the most effective vaccines with respect to the ability to permanently induce the regression of established TC-1. Only 12% of the Vac-SigE7Lamp treated mice were tumor free while 37% of the Vac-LLO-E7 and Lm-LLO-E7 mice were tumor free. All other mice were dead.

Thus, expression of the antigen as a fusion protein with a non-hemolytic truncated form of listeriolysin O in host cell systems in *listeria* and host cell systems other than *listeria* results in enhanced immunogenicity of the antigen. While comparative experiments were performed with vaccinia, a multitude of other plasmids and expression systems which can be used to express these fusion proteins are known. For example, bacterial vectors useful in the present invention include, but are not limited to *Salmonella* sp., *Shigella* sp., BCG, *L. monocytogenes* and *S. gordonii*. In addition the fusion proteins can be delivered by recombinant bacterial vectors modified to escape phagolysosomal fusion and live in the cytoplasm of the cell. Viral vectors useful in the present invention include, but are not limited to, Vaccinia, Avipox, Adenovirus, AAV, Vaccinia virus NYVAC, Modified vaccinia strain Ankara (MVA), Semliki Forest virus, Venezuelan equine encephalitis virus, herpes viruses, and retroviruses. Naked DNA vectors can also be used.

As a non-limiting example, a commercially available plasmid can be used in the present invention. Such plasmids are available from a variety of sources, for example, Invitrogen (La Jolla, Calif.), Stratagene (La Jolla, Calif.), Clontech (Palo Alto, Calif.), or can be constructed using methods well known in the art. A commercially available plasmid such as pCR2.1 (Invitrogen, La Jolla, Calif.), which is a prokaryotic expression vector with an prokaryotic origin of replication and promoter/regulatory elements to facilitate expression in a prokaryotic organism.

The present invention further comprises transforming such a *Listeria* strain with a plasmid comprising, inter alia, an isolated nucleic acid encoding a truncated ActA protein, or fragment thereof, and an antigen. As a non-limiting example, if an *L. monocytogenes* vaccine strain comprises a deletion in the prfA gene or the actA gene, the plasmid can comprise a prfA or actA gene in order to complement the mutation, thereby restoring function to the *L. monocytogenes* vaccine strain. As described elsewhere herein, methods for transforming bacteria are well known in the art, and include calcium-chloride competent cell-based methods, electroporation methods, bacteriophage-mediated transduction, chemical, and physical transformation techniques (de Boer et al, 1989, Cell 56:641-649; Miller et al, 1995, FASEB J., 9:190-199; Sambrook et al. 1989, Molecular Cloning: A Laboratory Manual, Cold Spring Harbor Laboratory, New York; Ausubel et al., 1997, Current Protocols in Molecular Biology, John Wiley & Sons, New York; Gerhardt et al., eds., 1994, Methods for General and Molecular Bacteriology, American Society for Microbiology, Washington, D.C.; Miller, 1992, A Short Course in Bacterial Genetics, Cold Spring Harbor Laboratory Press, Cold Spring Harbor, N.Y.).

The plasmid of the present invention comprises a promoter/regulatory sequence operably linked to a gene encoding a fusion protein, antigen, amino acid metabolism gene, or combinations thereof.

Plasmids and other expression vectors useful in the present invention are described elsewhere herein, and can include such features as a promoter/regulatory sequence, an origin of replication for gram negative and/or gram positive bacteria, and an isolated nucleic acid encoding a fusion protein. Further, the isolated nucleic acid encoding a fusion protein will have its own promoter suitable for driving expression of such an isolated nucleic acid. Promoters useful for driving expression in a bacterial system are well known in the art, and include bacteriophage lambda, the bla promoter of the beta-lactamase gene of pBR322, and the CAT promoter of the chloramphenicol acetyl transferase gene of pBR325. Further examples of prokaryotic promoters include the major right and left promoters of bacteriophage lambda ($P_L$ and $P_R$), the trp, recA, lacZ, lacd, and gal promoters of *E. coli*, the alpha-amylase (Ulmanen et al, 1985. J. Bacteriol. 162:176-182) and the S28-specific promoters of *B. subtilis* (Gilman et al, 1984 Gene 32:11-20), the promoters of the bacteriophages of *Bacillus* (Gryczan, 1982, In: The Molecular Biology of the Bacilli, Academic Press, Inc., New York), and *Streptomyces* promoters (Ward et al, 1986, Mol. Gen. Genet. 203:468-478). Additional prokaryotic promoters contemplated in the present invention are reviewed in, for example, Glick (1987, J. Ind. Microbiol. 1:277-282); Cenatiempo, (1986, Biochimie, 68:505-516); and Gottesman, (1984, Ann. Rev. Genet. 18:415-442). Further examples of promoter/regulatory elements contemplated in the present invention include, but are not limited to the Listerial prfA promoter (GenBank Acc. No. Y07639), the Listerial hly promoter (GenBank Acc. No. X15127), and the Listerial p60 promoter (GenBank Acc. No. AY126342), or fragments thereof.

Proper expression in a prokaryotic cell also requires the presence of a ribosome binding site upstream of the gene-encoding sequence. Such ribosome binding sites are disclosed, for example, by Gold, L., et al (1981, Ann. Rev. Microbiol. 35:365-404).

Accordingly, the present invention provides methods for enhancing the immunogenicity of an antigen via fusion of the antigen to a non-hemolytic truncated form of listeriolysin O or ΔLLO. In one embodiment, the antigen is fused to the PEST-like amino acid sequence, SEQ ID NO:1, of LLO. The present invention further provides methods and compositions for enhancing the immunogenicity of an antigen by fusing the antigen to a truncated ActA protein, or fragment thereof. This is because, as demonstrated by the data disclosed herein, an antigen fused to an ActA protein, when administered to an animal, results in, among other things, an immune response that clears existing tumors and results in the induction of antigen specific cytotoxic lymphocytes.

The present invention also provides methods for enhancing cell mediated and anti-tumor immunity and compositions with enhanced immunogenicity which comprise a PEST-like amino acid sequence derived from a prokaryotic organism fused to or embedded within an antigen. The PEST-like sequence can be fused to either the amino terminus or the carboxy terminus of the antigen. As demonstrated herein, fusion of an antigen to the PEST-like sequence of *L. monocytogenes* enhanced cell mediated and anti-tumor immunity of the antigen. It is believed that fusion of an antigen to other PEST-like sequences derived from other prokaryotic organisms will also enhance immunogenicity of the antigen. PEST-like sequence of other prokaryotic organism can be identified routinely in accordance with methods such as described by, for example Rechsteiner and Rogers (1996, Trends Biochem. Sci. 21:267-271) for *L. monocytogenes*. Alternatively, PEST-like amino acid sequences from other prokaryotic organisms can also be identified based by this method. Other prokaryotic organisms wherein PEST-like amino acid sequences would be expected to include, but are not limited to, other *Listeria* species. For example, the *L. monocytogenes* protein ActA contains four such sequences. These are KTEEQPSEVNTGPR (SEQ ID NO:2), KASVTDTSEGDLDSSMQSADEST PQPLK (SEQ ID NO:3), KNEEVNASDFPPPPTDEELR (SEQ ID NO:4), and RGGIPTSEEFSSLNSGDFTDDENS-ETTEEEIDR (SEQ ID NO:5). Also Streptolysin O from *Streptococcus* sp. contain a PEST-LIKE sequence. For example, *Streptococcus pyogenes* Streptolysin O comprises the PEST-like sequence KQNTASTETTTTNEQPK (SEQ ID NO:6) at amino acids 35-51 and *Streptococcus equisimilis* Streptolysin O comprises the PEST-like sequence KQNTAN-TETTTTNEQPK (SEQ ID NO:7) at amino acids 38-54. Further, the PEST-like sequence can be embedded within the antigenic protein. Thus, for purposes of the present invention, by "fusion" it is meant that the antigenic protein comprises both the antigen and the PEST-like amino acid sequence either linked at one end of the antigen or embedded within the antigen.

In a preferred embodiment, fusion proteins of the present invention are produced recombinantly via a plasmid which encodes either a truncated form of the listeriolysin O comprising the PEST-like amino acid sequence of *L. monocytogenes* or a PEST-like amino acid sequence derived from another prokaryotic organism and the antigen. However, the antigen may also be chemically conjugated to the truncated form of listeriolysin O comprising the PEST-like amino acid sequence of *L. monocytogenes* or a PEST-like amino acid sequence derived from another prokaryotic organism. For purposes of the present invention, by "antigen" it is meant to include the native antigen gene or gene product or truncated versions of these that include identified T cell epitopes. These fusion proteins can then be incorporated into vaccines for administration to animals, preferably humans, to invoke an enhanced immune response against the antigen of the fusion protein. In one embodiment, the fusion proteins of the present invention are delivered as DNA vaccines, RNA vaccines or replicating RNA vaccines. As will be obvious to those of skill in the art upon this disclosure, vaccines comprising the fusion proteins of the present invention are particularly useful in the prevention and treatment of infectious and neoplastic diseases.

These vaccines may further comprise adjuvants. Examples of adjuvants useful in these vaccines include, but are not limited to, unmethylated CpG, quill glycosides, CFA, QS21, monophosphoryl lipid A, liposomes, and bacterial mitogens and toxins.

The present invention further comprises administering to an animal, preferably a mammal, even more preferably a human, an effective amount of a composition comprising a Listeria vaccine strain. The construction of such strains is detailed elsewhere herein. The composition comprises, among other things, a pharmaceutically acceptable carrier. That is, as detailed herein, the composition includes a Listeria vaccine strain comprising a truncated ActA protein, or fragment thereof, fused to an antigen, and a pharmaceutically acceptable carrier.

Pharmaceutically acceptable carriers that are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey), the disclosure of which is incorporated by reference in its entirety herein.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease being treated or prevented, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer the receptor protein and/or a nucleic acid encoding the same according to the methods of the invention.

Compounds which are identified using any of the methods described herein may be formulated and administered to a mammal for treatment of infectious diseases and cancers, are now described.

The invention encompasses the preparation and use of pharmaceutical compositions comprising a compound useful for treatment of a wide variety of disorders such as lymphomas, myelomas, carcinomas, melanomas, gliomas, infectious diseases, autoimmune disorders, and the like.

Such a pharmaceutical composition can consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to an animal, preferably a human, will vary depending upon any number of factors, including but not limited to, the type of animal and type of disease state being treated, the age of the animal and the route of administration.

The compound can be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, and the like. Preferably, the compound is, but need not be, administered as a bolus injection that provides lasting effects for at least one day following injection. The bolus injection can be provided intraperitoneally.

The present invention encompasses various kits which comprise a compound, including a *Listeria* vaccine strain comprising an antigen fused to a truncated ActA protein, or a fragment thereof, an antigen fused to a truncated ActA protein, or a fragment thereof, an applicator, and an instructional material which describes use of the compound to perform the methods of the invention. Although model kits are described below, the contents of other useful kits will be apparent to the skilled artisan in light of the present disclosure. Each of these kits is contemplated within the present invention.

In one aspect, the invention includes a kit for eliciting an enhanced immune response to an antigen. The kit is used in the same manner as the methods disclosed herein for the present invention. Briefly, the kit may be used to administer an *Listeria* vaccine strain comprising an antigen fused to a truncated ActA protein. Additionally, the kit comprises an applicator and an instructional material for the use of the kit. These instructions simply embody the examples provided herein.

The kit further includes a pharmaceutically-acceptable carrier. The composition is provided in an appropriate amount as set forth elsewhere herein. Further, the route of administration and the frequency of administration are as previously set forth elsewhere herein.

In another aspect, the invention includes a kit for eliciting an enhanced immune response to an antigen. The kit is used in the same manner as the methods disclosed herein for the present invention. Briefly, the kit may be used to administer an an antigen fused to a truncated ActA protein. Additionally, the kit comprises an applicator and an instructional material for the use of the kit. These instructions simply embody the examples provided herein.

The kit further includes a pharmaceutically-acceptable carrier. The composition is provided in an appropriate amount as set forth elsewhere herein. Further, the route of administration and the frequency of administration are as previously set forth elsewhere herein.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein. Sewell et al. (2004, Arch. Otolaryngol. Head Neck Surg., 130: 92-97) is hereby incorporated by reference in its entirety herein.

Example 1

Tumor Cell Lines

TC-1 is a lung epithelial cell from C57BL/6 mice immortalized by HPV-16 E6 and E7 and transformed by pVEJB expressing activated human c-HA-ras. C3 is a mouse embryo cell frp, C57BL/6 mice immortalized with the complete genome of HPV 16 and transformed with pEJ-ras. EL-4/E7 is the thymoma EL-4 retrovirally transduced with E7.

Example 2

Comparison of Efficacy of Lm-GG/E7, Lm-AZ/E7 and Vac-SigE7Lamp

TC-1 ($1\times10^5$) or C-3 ($5\times10^5$) tumor cells were implanted subcutaneously in mice and allowed to grow for 7 to 9 days by which time they were palpable (about 5 mm in size). Mice were then immunized i.p. with one of three constructs, Vac-SigE7Lamp ($10^7$ PFU), Lm-E7 ($10^6$ CFU) or Lm-LLO-E7 ($10^7$ CFU). Animals received Lm-LLO-E7 and LM-E7 on days 7 and 14. Surviving mice were re-challenged with $10^5$ TC-1 on day 43.

Example 3

Comparison of Efficacy of Vac-LLO-E7, Vac-E7 and Vac-SigE7Lamp

Four groups of 8 mice were implanted with $10^5$ cells of TC-1. After 7 days the tumors were approximately 4 mm in size. One group of mice was untreated. Each of the other groups received $10^7$ PFU of either Vac-E7, Vac-LLO-E7 or Vac-Sig-E7-lamp 7. A booster dose was administered on day 14.

Example 4

Comparison of Efficacy of Vac-LLO-E7 and Lm-LLO-E7 with Various Other Vectors

TC-1 tumor cells ($2\times10^5$) were implanted s.c. on the left flank in 96 C57BL/6 mice and allowed to grow for 7 days. The mice were divided into groups of 8 mice and each group was treated with one of the following vaccine: naive (no vaccine); Vac SigE7Lamp, $10^7$ PFU, i.p.; Vac-LLO-E7, $10^7$ PFU, i.p.; or Lm-LLO-E7, $10^7$ PFU, i.p. The animals received a booster immunization one week later. Tumor growth was followed every two days by caliper measurement and recorded as the average of the narrowest and longest surface length. Immune parameters were also determined.

Example 5

Construction of Lm-LLOPEST-E7

The LLO-PEST-E7 fragment can be constructed via SOEing PCR. In Step 1 of this method, PCR reaction 1 uses primer pair GG-36/GG-78 or GG-77/AZ-9 with pGG-55 for the template. PCR reaction 2 uses LLO-PEST and E7 products from the first reaction as templates and the primers GG-36 and AZ-9.

```
                                                 (SEQ ID NO:8)
GG-36: 5'-GCTAGCCCTCCTTTGATTAGTATATTC-3', (SEQ ID NO:9)
GG-77: 5'-GCGGATGAAATCGATAAGCATGGAGATACACCTACA-3', (SEQ ID NO:10)
GG-78: 3'-CGCCTACTTTAGCTATTCGTACCTCTATGTGGATGT-5'

(SEQ ID NO:11)
AZ-9:  3'-GAGTCTTTGGTATTGGGCCC-5'.
```

In step 2, the final SOEing PCR product of 0.7 Kb is ligated into the TA vector pCR2.1.

In step 3, the LLO-PEST-E7 is digested from the plasmid with the enzyme NheI for 2 hours followed by ethanol precipitation and the enzyme XmaI overnight. The prfA fragment from pGG-49 is digested with the enzyme SalI for 2 hours followed by ethanol precipitation and XmaI overnight. pDP-2028 is digested with SalI and XbaI for 2 hours followed by ethanol precipitation and resuspension in Tris:EDTA (TE). The fragment can be stored overnight at 4° C.

In step 4, the 0.7 Kb LLO-PEST-E7, 1.0 Kb prfA and the 9.7 Kb plasmid are ligated. This plasmid is then used to transform XFL-7. Secretion of a 15 Kb fragment can be verified via Western blot. Efficacy is verified against TC-1 tumors.

Alternatively, a chromosomal integrant can be generated by amplifying the LLO-PEST-E7 fragment using the primer AZ-B (5'-GCTCTAGATTATGGTTTCT GAG-3'; SEQ ID NO:12) to install a 3' XbaI site and primer ZY-3 (5'-GGGG-TACCCT CCTTTGATTAGTATAT-3'; SEQ ID NO:13) to install a 5' KpnI site. pZY-37 and the LLO-PEST-E7 fragment are digested with KpnI and XbaI separately or in NEB buffer 2+BSA overnight. The fragment is ligated into pZY-37 and the following protocol for chromosomal integration is followed. Secretion and efficacy are verified as described above.

Example 6

Construction of Lm-actA-E7

*L. monocytogenes* strain XFL7 (a prfA negative *L. monocytogenes* 10403s provided by Dr. Jeff Miller, University of California Los Angeles, Los Angeles, Calif.) was the organism used in the cloning studies of the construct Lm-actA-E7. Lm-actA-E7 is a recombinant strain of *L. monocytogenes*, comprising a plasmid that express the E7 protein fused to a truncated version of the actA protein.

Figure 7:
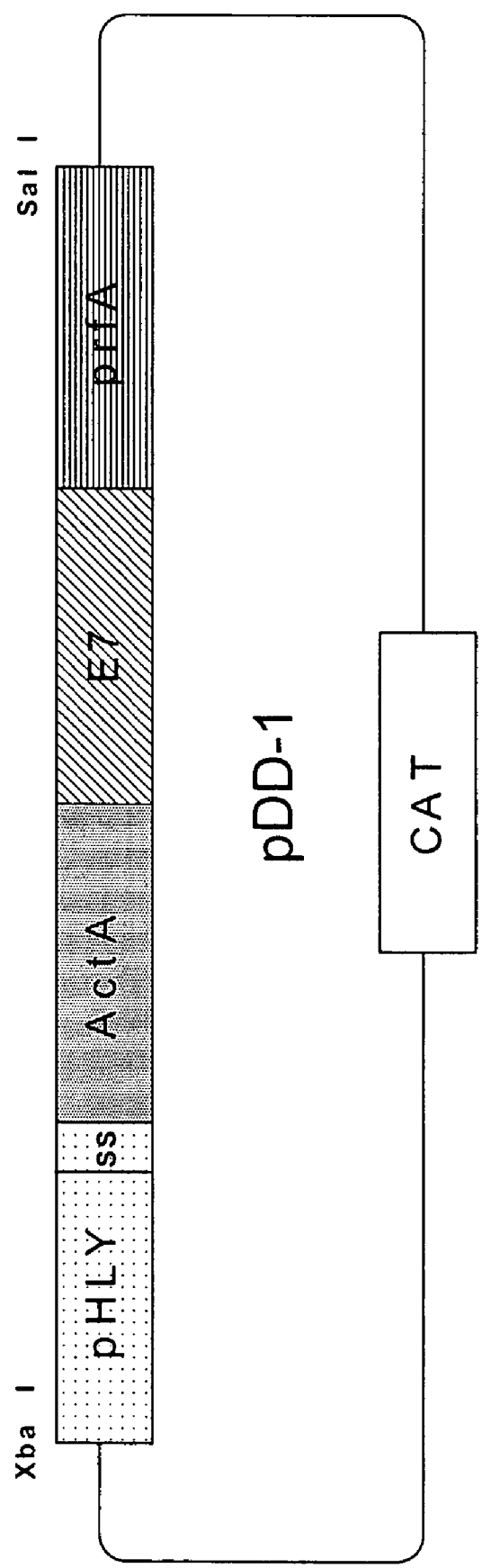
FIG. 7 depicts a schematic representation of the pActA-E7 expression system used to express and secrete E7 from recombinant *Listeria* bacteria. The hly promoter (pHLY) drives expression, the prfA gene is used to select retention of the plasmid by recombinant *Listeria* in vivo.

Lm=actAE7 was generated by introducing a plasmid vector pDD1 constructed by modifying pDP-2028 (Ikonomidis et al., 1994, J. Exp. 180:2209-2218) into *L. monocytogenes*. The pDD-1 plasmid comprises an expression cassette expressing a copy of the 310 bp hly promoter and the hly signal sequence (ss), (this gene drives the expression and secretion of the actA-E7 gene product), 1170 bp of the actA gene that comprises four PEST sequences (the truncated ActA polypeptide consists of the first 390 amino acids of the molecule, a copy of the 300 bp E7 gene (HPV tumor protein), a copy of the 1019 bp prfA gene (controls expression of the virulence genes) and copy of the CAT gene (chloramphenicol resistance gene) for selection of transformed bacteria clones (FIG. 7).

The hly promoter (pHly) and gene fragment were PCR amplified from pGG55 (pLLO-E7, Gunn et al., 2001, J. Immunol. 167:6471-6479) using primer 5'-GGGG TCTAGACCTCCTTTGATTAGTATATTC-3' (Xba I site is underlined) (SEQ ID NO:14) and primer 5'-ATCTTCGC-TATCTGTCGCCGCGGCGC GTGCTTCAGTTTGT-TGCGC-'3 (Not I site is underlined. The first 18 nucleotides are the ActA gene overlap). (SEQ (SEQ ID NO:15). The actA gene was PCR amplified from the *Listeria monocytogenes* 10403s wildtype genome using primer 5'-GCGCAACAAA CTGAAGCAGCGGCCGCGGCGACAGAT-AGCGAAGAT-3' (SEQ ID NO:16) and primer 5'-TGTAG-GTGTATCTCCATGCTCGAGAGCTAGGC-GATCAATTTC-3' (SEQ ID NO:17). The E7 gene was PCR amplified from pGG55 (pLLO-E7) using primer 5'-GGAAT-TGATCGCCTAGCTCTCGAGCATG-GAGATACACCTACA-3' (SEQ ID NO:18) and primer 5'-AAACGGATTTATTTAGATCCCGGGTTATG GTTTCTGAGAACA-3' (SEQ ID NO:19). The prfA gene was PCR amplified from the *Listeria monocytogenes* 10403s wildtype genome using primer 5'-TGTTCTCA GAAAC-CATAACCCGGGATCTAAATAAATCCGTTT-3' (SEQ ID NO:20) and primer 5'-GGGGGTCGACCAGCTCTTCTTG-GTGAAG-3' (SEQ ID NO:21). The hly promoter was fused to the actA gene (pHly-actA) was PCR generated and amplified from purified pHly DNA and purified actA DNA using the pHly primer (upstream) 5'-GGGG TCTAGACCTCCTTTGATTAGTATATTC-3' (SEQ ID NO:14) and acta primer (downstream) 5'-TGTAGGTG-TATCTCCATGCTCGAGAGCTAGGCGATCAATTTC-3' (SEQ ID NO:17).

The E7 gene fused to the prfA gene (E7-prfA) was PCR generated and amplified from purified E7 DNA and purified prfA DNA using the E7 primer (upstream) GGAAT-TGATCGCCTAGCTCTCGAGCATG-GAGATACACCTACA-3' (SEQ ID NO:18) and prfA gene primer (downstream) 5'-GGGGGTCGACCAGCTCT-TCTTG GTGAAG-3' (SEQ ID NO:21).

The pHly-actA fusion product fused to the E7-prfA fusion product is PCR generated and amplified from purified fused pHly-actA DNA product and purified fused E7-prfA DNA product using the pHly primer (upstream) 5'-GGGGTCTA-GACCTCCTT TGATTAGTATATTC-3' (SEQ ID NO:14) and prfA gene primer (downstream) 5'-GGGGGTCGAC-CAGCTCTTCTTGGTGAAG-3' (SEQ ID NO:21) and ligated into pCRII (Invitrogen, La Jolla, Calif.). Competent *E. coli* (TOP10'F, Invitrogen, La Jolla, Calif.) were transformed with pCRII-ActAE7. After lysis and isolation, the plasmid was screened by restriction analysis using BamHI (expected fragment sizes 770 bp and 6400 bp (or when the insert was reversed into the vector: 2500 bp and 4100 bp)) and BstXI (expected fragment sizes 2800 bp and 3900 bp) and also screened with PCR analysis using the pHly primer (upstream) 5'-GGGGTCTAGACCTCCTTTGATTAGTATATTC-3' (SEQ ID NO:14) and the prfA gene primer (downstream) 5'-GGGGGTCGACCAGC TCTTCTTGGTGAAG-3' (SEQ ID NO:21).

The pHly-ActA-E7-PrfA DNA insert was excised from pCRII by double digestion with Xba I and Sal I and ligated into pDP-2028 also digested with Xba I and Sal I. After transforming TOP10'F competent *E. coli* (Invitrogen, La Jolla, Calif.) with expression system pActAE7, chloramphenicol resistant clones were screened by PCR analysis using the pHly primer (upstream) 5'-GGGGTCTAGACCTC-CTTTGATT AGTATATTC-3' (SEQ ID NO:14) and the prfA gene primer (downstream) 5'-GGGGGTCGACCAGCTCT-TCTTGGTGAAG-3' (SEQ ID NO:21). A clone comprising pActAE7 was grown in brain heart infusion medium (with chloramphenicol (20 µg/ml), Difco, Detroit, Mich.) and pActAE7 was isolated from the bacteria cell using a midiprep DNA purification system kit (Promega, Madison, Wis.). A prfA-negative strain of penicillin-treated *Listeria* (strain XFL-7) was transformed with expression system pActAE7, as described in Ikonomidis et al. (1994, J. Exp. Med. 180: 2209-2218) and clones were selected for the retention of the plasmid in vivo. Clones were grown in brain heart infusion with chloramphenicol (20 µg/ml) at 37° C. Bacteria were frozen in aliquots at −80° C.

Example 7

Immunoblot Verification of Antigen Expression

Figure 8:
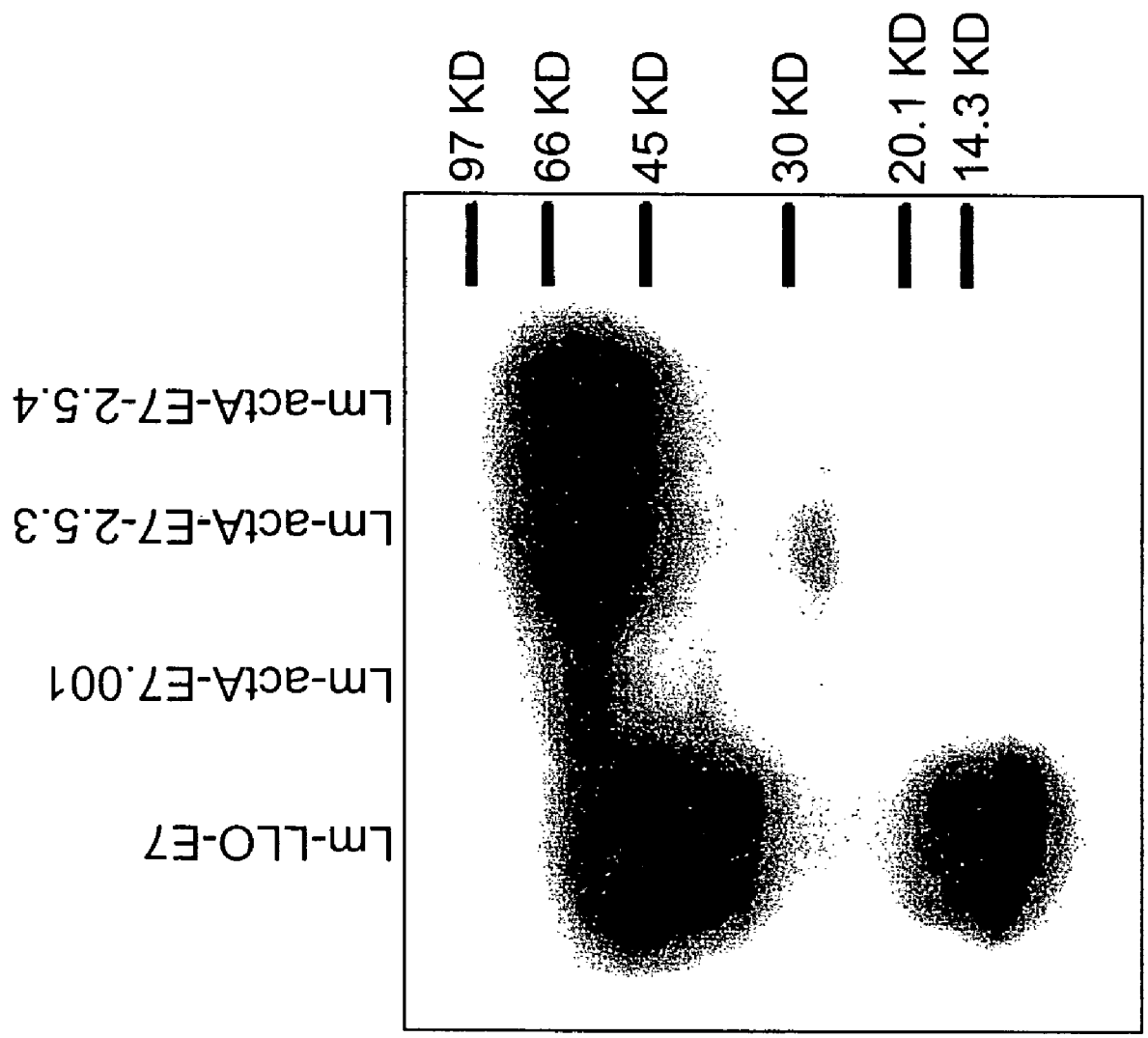
FIG. 8 depicts a Western blot demonstrating that Lm-ActA-E7 secretes E7. Lane 1 depicts Lm-LLO-E7, lane 2 depicts Lm-ActA-E7.001, lane 3 depicts Lm-ActA-E7-2.5.3, lane 4 depicts Lm-ActA-E7-2.5.4.

In order to verify that Lm-ActA-E7 secretes a fusion protein of the correct molecular weight (about 64 kD), recombinant bacteria were grown overnight at 37° C. in Luria-Bertoni broth and pelleted. About 18 milliliters of supernatant from each culture was TCA precipitated and E7 expression was analyzed by Western blot. Specifically, clones 0.001' 2.5.3 and 2.5.4 were grown in Luria-Bertoni medium (Difco, Detroit, Mich.) at 37° C. Supernatants were TCA precipitated and resuspended in 1× sample buffer with 0.1N NaOH. Identical amounts of each TCA precipitated supernatant were loaded on 4-20% Tris-glycine SDS-PAGE gel (NOVEX, San Diego, Calif.). The gel was transferred to polyvinylidene difluoride membrane and probed with anti-E7 mAb at a dilution of 1:2500 (Zymed Laboratories, South San Francisco, Calif.). The secondary Ab was HRP-conjugated anti-mouse IgG, diluted 1:5000 (Amersham Pharmacia Biotech, Little Chalfont, U.K.). Blots were developed with Amersham ECL detection reagents and exposed to Hyperfilm (Amersham Pharmacia Biotech) (FIG. 8).

Example 8

Anti-Tumor Immunity of Lm-ActA-E7

Figure 9:
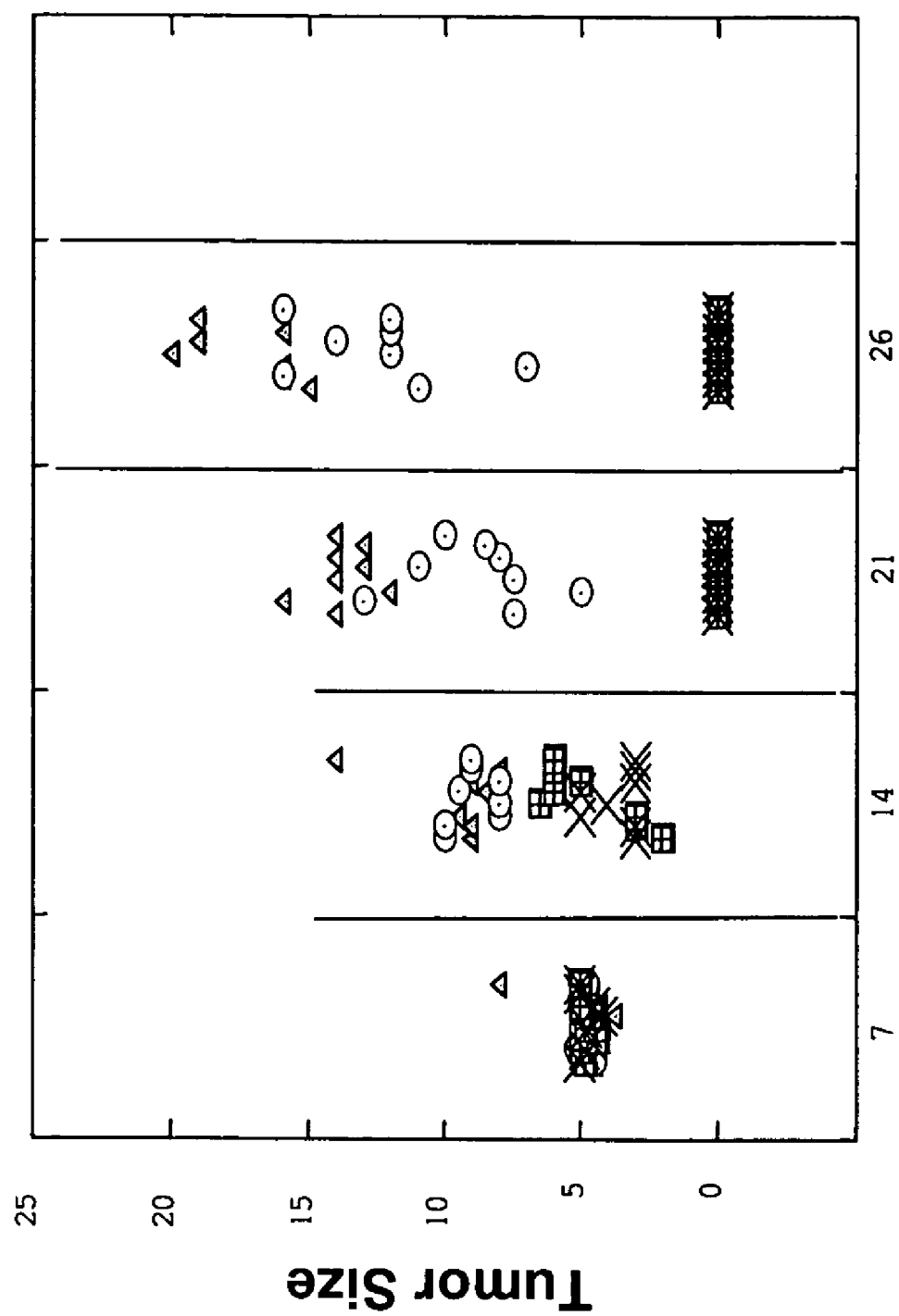
FIG. 9 is a graph depicting tumor size in mice administered Lm-ActA-E7 (rectangles), Lm-E7 (ovals), Lm-LLO-E7 (X), and naive mice (non-vaccinated; solid triangles).

To compare the anti-tumor immunity induced by Lm-ActA-E7 versus Lm-LLO-E7 and Lm-E7, 2×10$^5$ TC-1 tumor cells were implanted subcutaneously in mice and allowed to grow for 7 days by which time they were palpable (approximately 5 millimeters in size). Mice were then immunized intraperitoneally with one LD$_{50}$ of either Lm-ActA-E7 (5×10$^8$ CFU), Lm-LLO-E7 (10$^8$ CFU) or Lm-E7 (10$^6$ CFU) on days 7 and 14 following TC-1 cell implantation. Tumor growth was measured periodically with calipers. By day 26 all of the animals in the Lm-LLO-E7 and Lm-ActA-E7 were tumor free and remained so whereas all of the naïve animals and the animals that were immunized with Lm-E7 grew large tumors (FIG. 9).

Example 9

Ability of Lm-ActA-E7 to Enhance E7 Specific Immunity

To analyze the ability of Lm-ActA-E7 to enhance antigen specific immunity, 500 µl of MATRIGEL™, comprising 100 µl of 2×10$^5$ TC-1 tumor cells in phosphate buffered saline plus 400 µl of MATRIGEL™ (BD Biosciences, Franklin Lakes, N.J.) were implanted subcutaneously on the left flank of 12 C57BL/6 mice. The mice were divided into 4 groups, 3 mice per group. On day 7, 14 and 21 each group of mice was administered (intraperitoneally) either naive (untreated), Lm-LLO-E7 (1×10$^7$ CFU), Lm-E7 (1×10$^6$ CFU), or Lm ActA E7 (2×10$^8$ CFU). Spleens and tumors were harvested 7 days following the last immunization on day 21. Tumor MATRIGELs were removed from the mice and placed in tubes containing 2 milliliters of RP 10 medium on ice and incubated at 4° C. overnight. The tumors were then minced with forceps, cut into 2 millimeter blocks and treated with 3 ml of enzyme mixture (0.2 mg/ml collagenase-P, 1 mg/ml DNAse-1 in PBS) and incubated at 37° C. for 1 hour. The tissue suspension was then filtered through nylon mesh, washed with 5% fetal bovine serum+0.05% of NaN$_3$ in PBS for tetramer and IFN-gamma staining.

Figure 10:
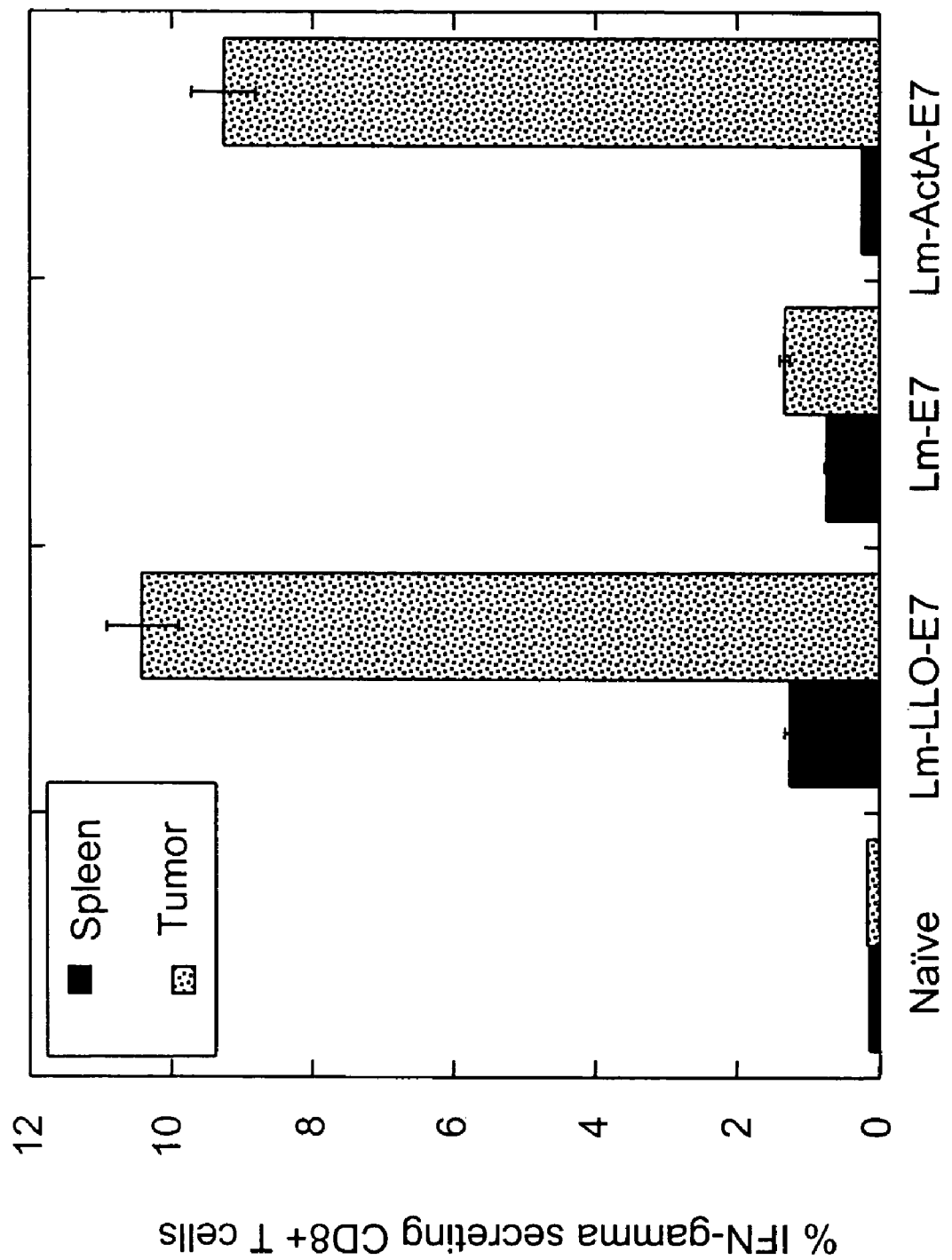
FIG. 10 is a graph depicting the induction of E7 specific IFN-gamma secreting $CD8^+$ T cells in the spleens and tumors of mice administered TC-1 tumor cells and subsequently administered Lm-E7, Lm-LLO-E7, Lm-ActA-E7 or no vaccine (naive).

Splenocytes and tumor cells were incubated with 1 µm E7 peptide for 5 hours in the presence of the Golgi transport inhibitor brefeldin A at a density of 10$^7$ cells/ml. Cells were washed twice and incubated in 50 µl of anti-mouse Fc receptor supernatant (2.4 G2) for 1 hour or overnight at 4° C. Cells were stained for surface molecules CD8 and CD62L, permeabilized, fixed using the permeabilization kit Golgi-stop or Golgi-Plug (Pharmingen, San Diego, Calif.) and then stained for IFN-gamma. Typically, 500,000 events were acquired using two-laser flow cytometer FACS Calibur and analyzed using Cellquest Software (Becton Dickinson, Franklin Lakes, N.J.). The percentage of IFN-gamma secreting cells within the activated (CD62L low) CD8$^+$ T cells was calculated. CD8$^+$ T cells secreting IFN-gamma infiltrate the tumors of mice administered Lm-LLO-E7 and Lm-ActA-E7 to a much greater degree than in mice administered Lm-E7 or naive mice (FIG. 10).

Figure 11:
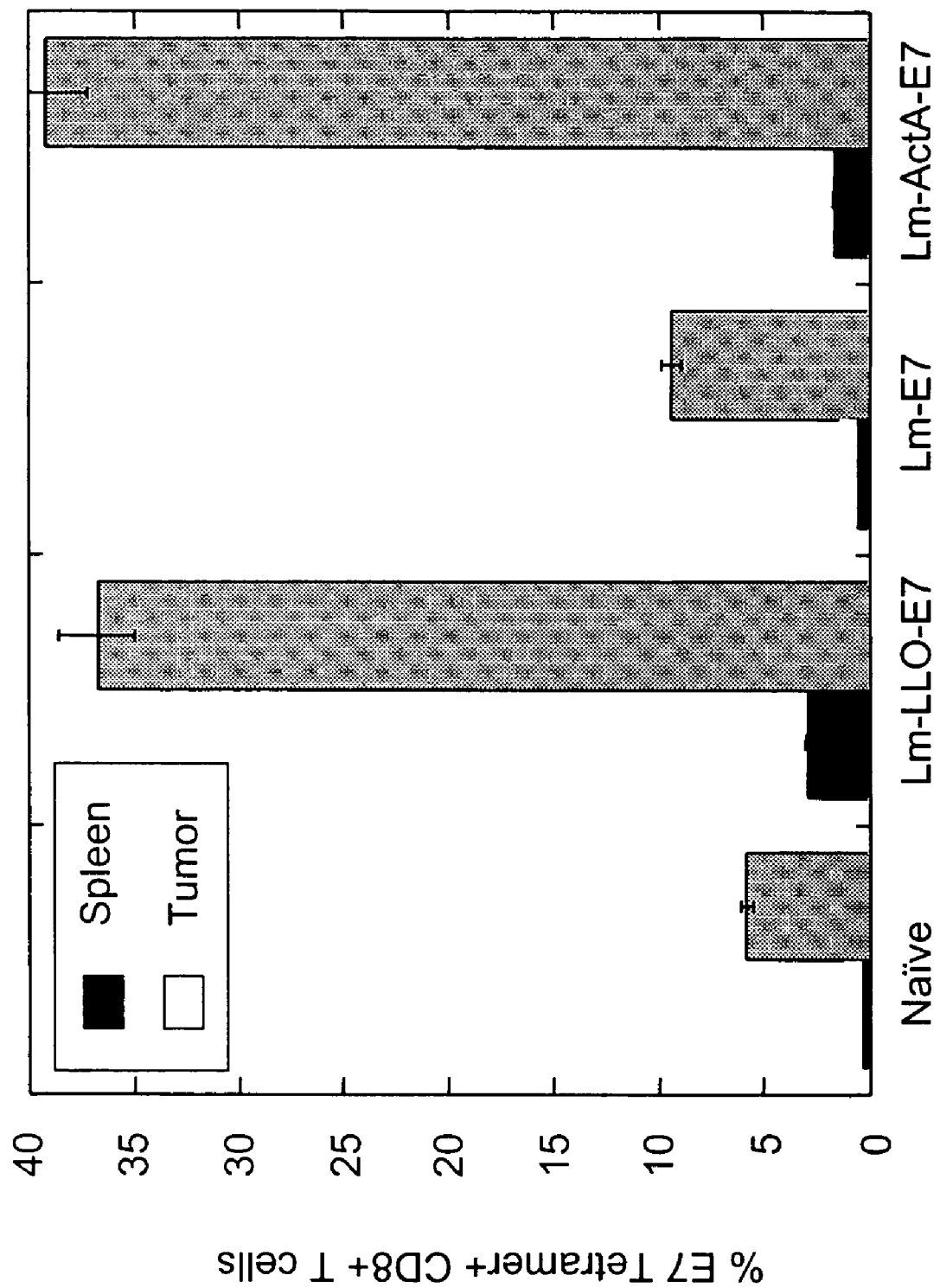
FIG. 11 is a graph depicting the induction and penetration of E7 specific $CD8^+$ cells in the spleens and tumors of mice administered TC-1 cells and subsequently administered a recombinant *Listeria* vaccine (naïve, Lm-LLO-E7, Lm-E7, Lm-ActA-E7).

For tetramer staining, H-2D$^b$ tetramer was loaded with phycoerythrin (PE) conjugated E7 peptide (RAHYNIVTF, SEQ ID NO:22) and stained at room temperature for 1 hour and then stained with anti-allophycocyanin (APC) conjugated MEL-14 (CD62L) and FITC-conjugated CD8β on ice for 30 min. Cells were analyzed comparing tetramer$^+$ CD8$^+$ CD62L$^{low}$ cells generated by the different recombinant *Listeria* in the spleen and in the tumor. Lm-ActA-E7 immunized mice produce a greater number of tumor-infiltrating E7 tetramer specific CD8$^+$ cells than mice administered Lm-LLO-E7, and a far greater number of tumor-infiltrating E7 tetramer specific CD8$^+$ cells than mice administered Lm-E7 and naive mice (FIG. 11).

The data disclosed herein demonstrate a distinct correlation between the numbers of CD8$^+$ T cells infiltrating the tumors and the ability of the constructs to kill the tumor. Thus, Lm-LLO-E7 and Lm-ActA-E7 are equally effective at inducing the regression of TC-1 and also induce the largest number of infiltrating CD8$^+$ T cells measured as E7 specific IFN-gamma secreting cells or as E7 specific tetramer positive cells.

The disclosures of each and every patent, patent application, and publication cited herein are hereby incorporated by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A *Listeria monocytogenes* vaccine strain comprising an antigen fused to a truncated ActA protein, wherein said truncated ActA protein consists of amino acids 1-390 of said ActA protein; wherein said truncated ActA protein comprises a PEST-like sequence selected from the sequences set forth in SEQ ID No: 2-5; and wherein said antigen is selected from the group consisting of human papilloma virus (HPV) E6, HPV E7, Her-2/Neu, NY-ESO-1, human telomerase, WT-1, proteinase 3, TRP-2 and PSA antigen.

2. The *Listeria monocytogenes* vaccine strain of claim 1, wherein said truncated ActA protein consists of the sequence set forth in SEQ ID NO: 23.

3. The *Listeria monocytogenes* vaccine strain of claim 1, wherein said antigen and said truncated ActA protein are encoded by a vector.

4. The *Listeria monocytogenes* vaccine strain of claim 1, wherein said antigen and said truncated ActA protein are expressed from a promoter selected from the group consisting of an hly promoter, a prfA promoter, and a p60 promoter.

5. A kit for eliciting an enhanced immune response to an antigen, the kit comprising (a) the *Listeria monocytogenes* vaccine strain of claim 1 and (b) a pharmaceutically acceptable carrier, said kit further comprising an applicator, and an instructional material for use thereof.

6. A method of eliciting an enhanced immune response to an antigen, the method comprising administering to a subject an effective amount of a composition comprising a *Listeria monocytogenes* vaccine strain comprising said antigen fused to a truncated ActA protein, wherein said truncated ActA protein consists of amino acids 1-390 of said ActA protein; and wherein said truncated ActA protein comprises a PEST-like sequence selected from the sequences set forth in SEQ ID No: 2-5; and wherein said antigen is selected from the group consisting of human papilloma virus (HPV) E6, HPV E7, Her-2/Neu, NY-ESO-1, human telomerase, WT-1, proteinase 3, TRP-2, and PSA antigen.

7. The method of claim 6, wherein said subject is a human.

8. The method of claim 6, wherein said composition is suspended in a pharmaceutically acceptable carrier.

9. A *Listeria monocytogenes* vaccine strain comprising an antigen fused to a PEST-like sequence selected from the group consisting of the sequences set forth in SEQ ID No: 2-5, wherein said antigen is selected from human papilloma virus (HPV) E6, HPV E7, Her-2/Neu, NY-ESO-1, human telomerase, WT-1, proteinase 3, TRP-2, and PSA antigen.

10. The *Listeria monocytogenes* vaccine strain of claim 9, wherein said antigen and said PEST-like sequence are encoded by a vector.

11. The *Listeria monocytogenes* vaccine strain of claim 9, wherein said antigen and said PEST-like sequence are expressed from a promoter selected from the group consisting of an hly promoter, a prfA promoter, and a p60 promoter.

12. A kit for eliciting an enhanced immune response to an antigen, the kit comprising (a) the *Listeria monocytogenes* vaccine strain of claim 9 and (b) a pharmaceutically acceptable carrier, said kit further comprising an applicator, and an instructional material for use thereof.

13. A method of eliciting an enhanced immune response to an antigen, the method comprising administering to a subject an effective amount of a composition comprising a *Listeria monocytogenes* vaccine strain comprising said antigen fused to a PEST-like sequence selected from the group consisting of the sequences set forth in SEQ ID No: 2-5, wherein said antigen is selected from human papilloma virus (HPV) E6, HPV E7, Her-2/Neu, NY-ESO-1, human telomerase, WT-1, proteinase 3, TRP-2, and PSA antigen.

14. The method of claim 13, wherein said subject is a human.

15. The method of claim 13, wherein said composition is suspended in a pharmaceutically acceptable carrier.

16. The *Listeria monocytogenes* vaccine strain of claim 1, wherein said truncated ActA comprises a PEST-like sequence as set forth in SEQ ID No: 2.

17. The method of claim 6, wherein said truncated ActA comprises a PEST-like sequence as set forth in SEQ ID No: 2.

18. The *Listeria monocytogenes* vaccine strain of claim 9, wherein said PEST-like sequence is set forth in SEQ ID No: 2.

19. The method of claim 13, wherein said PEST-like sequence is set forth in SEQ ID No: 2.

* * * * *